(12) United States Patent
Park et al.

(10) Patent No.: US 10,144,972 B2
(45) Date of Patent: Dec. 4, 2018

(54) COMPOSITION FOR HOT-START REVERSE TRANSCRIPTION REACTION OR HOT-START REVERSE TRANSCRIPTION POLYMERASE CHAIN REACTION

(71) Applicant: BIONEER CORPORATION, Daejeon (KR)

(72) Inventors: Han Oh Park, Daejeon (KR); Jun Hee Lee, Daejeon (KR); Sora Choi, Yeongi-gun (KR); Hyun Seo Kim, Daejeon (KR)

(73) Assignee: BIONEER CORPORATION, Daejeon (KR)

(*) Notice: Subject to any disclaimer, the term of this patent is extended or adjusted under 35 U.S.C. 154(b) by 433 days.

(21) Appl. No.: 14/383,793

(22) PCT Filed: Mar. 11, 2013

(86) PCT No.: PCT/KR2013/001935
§ 371 (c)(1),
(2) Date: Sep. 8, 2014

(87) PCT Pub. No.: WO2013/133680
PCT Pub. Date: Sep. 12, 2013

(65) Prior Publication Data
US 2015/0044683 A1    Feb. 12, 2015

(30) Foreign Application Priority Data
Mar. 9, 2012  (KR) .................. 10-2012-0024676

(51) Int. Cl.
| | | |
|---|---|---|
| *C12P 19/34* | (2006.01) | |
| *C12Q 1/6886* | (2018.01) | |
| *C12Q 1/42* | (2006.01) | |
| *C12Q 1/48* | (2006.01) | |
| *C12Q 1/6848* | (2018.01) | |
| *C12Q 1/686* | (2018.01) | |

(52) U.S. Cl.
CPC ............ *C12Q 1/6886* (2013.01); *C12P 19/34* (2013.01); *C12Q 1/42* (2013.01); *C12Q 1/48* (2013.01); *C12Q 1/686* (2013.01); *C12Q 1/6848* (2013.01)

(58) Field of Classification Search
USPC ...................................... 435/6.12, 91.1, 91.2
See application file for complete search history.

(56) References Cited

U.S. PATENT DOCUMENTS

| | | | |
|---|---|---|---|
| 5,336,760 A | 8/1994 | Hardwick et al. | |
| 5,647,994 A | 7/1997 | Tuunanen et al. | |
| 5,702,590 A | 12/1997 | Bonte et al. | |
| 5,897,783 A | 4/1999 | Howe et al. | |
| 6,187,270 B1 | 2/2001 | Schmitt et al. | |
| 6,951,744 B2* | 10/2005 | Clark ................... | C12Q 1/6848 435/194 |
| 9,034,603 B2* | 5/2015 | Kim ....................... | C12Q 1/686 435/91.2 |
| 2010/0209973 A1 | 8/2010 | Kim et al. | |

FOREIGN PATENT DOCUMENTS

| | | |
|---|---|---|
| CN | 1522305 A | 8/2004 |
| EP | 0 691 541 A2 | 1/1996 |
| EP | 0726310 B1 | 7/2003 |
| KR | 10-0148239 B1 | 1/1996 |
| KR | 10-0292883 B1 | 9/2000 |
| KR | 10-2008-0032904 A | 4/2008 |
| KR | 10-2009-0043282 A | 5/2009 |
| KR | 10-0987352 B1 | 10/2009 |
| KR | 10-2010-0053011 A | 5/2010 |
| KR | 10-2011-0017226 A | 2/2011 |

OTHER PUBLICATIONS

State Intellectual Property Office of People's Republic of China, Communication dated Jul. 13, 2015, issued in counterpart Application No. 201380021339.3.
Biochemistry and Molecular Biology Experiment Course edited by Tianfeng HE, etc., Science Press; Jan. 31, 2012.
Japanese Patent Office, Communication dated Nov. 10, 2015 issued in counterpart application No. 2014-560860.
A. Malgoyre, et al., "Quantification of low-expressed mRNA using 5' LNA-containing real-time PCR primers", ScienceDirect, Biochemical and Biophysical Research Communication, 2007, pp. 246-252, vol. 354.
Bruno Fuchs, et al., "High Temperature cDNA Synthesis by AMV Reverse Transcriptase Improves the Specificity of PCR", Molecular Biotechnology, 1999, pp. 237-240, vol. 12.

(Continued)

*Primary Examiner* — Kenneth R Horlick
(74) *Attorney, Agent, or Firm* — Sughrue Mion, PLLC

(57) ABSTRACT

A composition for hot-start reverse transcription reaction and a composition for reverse transcription PCR are disclosed. The composition is obtained by adding pyrophosphate and pyrophosphatase to an aqueous solution containing reaction buffer solution, $MgCl_2$, four kinds of dNTPs, and reverse transcription polymerase in a single reaction tube. The composition for hot-start reverse transcription reaction is obtained by freezing or drying the composition. The composition show increased stability and long-term storage stability. Also, disclosed is a composition that additionally includes DNA polymerase, and, thus, enables a hot-start reverse transcription reaction and a PCR reaction to be sequentially performed. A method for amplifying a nucleic acid by using the composition. The composition of the invention can be conveniently and effectively used in multiplex reverse transcription PCRs or real-time quantitative reverse transcription PCR.

14 Claims, 18 Drawing Sheets
Specification includes a Sequence Listing.

(56) References Cited

OTHER PUBLICATIONS

Jiyoung Hong, et al., "Development of a highly sensitive real-time one step RT-PCR combined complementary locked primer technology and conjugated minor groove binder probe", Virology Journal, 2011, pp. 1-6, vol. 8, No. 330.

Rodney Mark Ratcliff, et al., "Sensitive Detection of RNA Viruses Associated with Gastroenteritis by a Hanging-Drop Single-Tube Nested Reverse Transcription-PCR Method", Journal of Clinical Microbiology, 2002, pp. 4091-4099, vol. 40, No. 11.

David J. Sharkey, et al., "Antibodies as Thermolabile Switches: High Temperature Triggering for the Polymerase Chain Reaction", Bio/Technology, 1994, pp. 506-509, vol. 12.

International Searching Authority, International Search Report of PCT/KR2013/001935, dated May 15, 2013. [PCT/ISA/210].

Patrick J. Finn et al., "Synthesis and application of charge-modified dye-labeled dideoxynucleoside-5'-triphosphates to 'direct-load' DNA sequencing", Nucleic Acids Research, 2002, vol. 30, No. 13, pp. 2877-2885.

Korean Intellectual Property Office, Communication dated May 23, 2016, issued in counterpart Application No. 10-2013-0025119.

\* cited by examiner

```
                          SEQUENCE LISTING

<160> NUMBER OF SEQ ID NOS: 15

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
ggaaggtgaa ggtcggagtc                                                    20

<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2
gccaaattcg ttgtcatacc                                                    20

<210> SEQ ID NO 3
<211> LENGTH: 22
<212> TYPE: DNA
<213> ORGANISM: Artificial
<220> FEATURE:
<223> OTHER INFORMATION: primer

<400> SEQUENCE: 3
cgtggaagga ctcatgacca ca                                                 22

<210> SEQ ID NO 4
<211> LENGTH: 20
<212> TYPE: DNA
<213> ORGANISM: Artificial
<220> FEATURE:
<223> OTHER INFORMATION: reverse primer

<400> SEQUENCE: 4
gccttggcag cgccagtaga                                                    20

<210> SEQ ID NO 5
<211> LENGTH: 23
<212> TYPE: DNA
<213> ORGANISM: Artificial
<220> FEATURE:
<223> OTHER INFORMATION: GAPDH probe

<400> SEQUENCE: 5
ctgtggatgg cccctccggg aaa                                                23

<210> SEQ ID NO 6
<211> LENGTH: 19
<212> TYPE: DNA
<213> ORGANISM: Artificial
<220> FEATURE:
<223> OTHER INFORMATION: primer

<400> SEQUENCE: 6
```

```
accgggtcct ttcttggat                                          19
```

<210> SEQ ID NO 7
<211> LENGTH: 20
<212> TYPE: DNA
<213> ORGANISM: Artificial
<220> FEATURE:
<223> OTHER INFORMATION: reverse primer

<400> SEQUENCE: 7

```
ccctatcagg cagtaccaca                                         20
```

<210> SEQ ID NO 8
<211> LENGTH: 20
<212> TYPE: DNA
<213> ORGANISM: Artificial
<220> FEATURE:
<223> OTHER INFORMATION: probe

<400> SEQUENCE: 8

```
cgtgccccccg cragactgct                                        20
```

<210> SEQ ID NO 9
<211> LENGTH: 20
<212> TYPE: DNA
<213> ORGANISM: Artificial
<220> FEATURE:
<223> OTHER INFORMATION: reverse primer having 6 mismatch nt at 5'end

<400> SEQUENCE: 9

```
gggggggcagg cagtaccaca                                        20
```

<210> SEQ ID NO 10
<211> LENGTH: 20
<212> TYPE: DNA
<213> ORGANISM: Artificial
<220> FEATURE:
<223> OTHER INFORMATION: reverse primer having 6 mismatch nt in the
      middle

<400> SEQUENCE: 10

```
ccctatttttt ttgtaccaca                                        20
```

<210> SEQ ID NO 11
<211> LENGTH: 20
<212> TYPE: DNA
<213> ORGANISM: Artificial
<220> FEATURE:
<223> OTHER INFORMATION: reverse primer having a single mismatch nt

<400> SEQUENCE: 11

```
ccctatcagg cagtcccaca                                         20
```

<210> SEQ ID NO 12
<211> LENGTH: 18
<212> TYPE: DNA
<213> ORGANISM: Artificial
<220> FEATURE:
<223> OTHER INFORMATION: primer

<400> SEQUENCE: 12

```
tttttttttt tttttttt                                           18
```

<210> SEQ ID NO 13
<211> LENGTH: 20
<212> TYPE: DNA

```
<213> ORGANISM: Artificial
<220> FEATURE:
<223> OTHER INFORMATION: primer

<400> SEQUENCE: 13
ggagcagatc aagaccctca                                              20

<210> SEQ ID NO 14
<211> LENGTH: 20
<212> TYPE: DNA
<213> ORGANISM: Artificial
<220> FEATURE:
<223> OTHER INFORMATION: reverse primer

<400> SEQUENCE: 14
ttgtccatgt tgcttcgagc                                              20

<210> SEQ ID NO 15
<211> LENGTH: 25
<212> TYPE: DNA
<213> ORGANISM: Artificial
<220> FEATURE:
<223> OTHER INFORMATION: probe

<400> SEQUENCE: 15
tgctgctcca ggaaccgtac cttgt                                        25
```

COMPOSITION FOR HOT-START REVERSE TRANSCRIPTION REACTION OR HOT-START REVERSE TRANSCRIPTION POLYMERASE CHAIN REACTION

CROSS REFERENCE TO RELATED APPLICATIONS

This application is a National Stage of International Application No. PCT/KR2013/001935 filed Mar. 11, 2013, claiming priority based on Korean Patent Application No. 10-2012-0024676, filed Mar. 9, 2012, the contents of all of which are incorporated herein by reference in their entirety.

TECHNICAL FIELD

The present invention relates to a composition for hot-start reverse transcription reaction or hot-start reverse transcription polymerase chain reaction.

BACKGROUND ART

Reverse transcription reactions are classified into reactions employing random primers, and reactions employing target-specific primers. In reverse transcription reactions for detection of a specific target, such as diagnostic kits for detection of RNA virus or the like, target-specific primers are generally used because they show higher sensitivity. In such reverse transcription reactions, specificity and sensitivity are determined by the high selectivity of primers that bind specifically to a target RNA sequence. However, because all components required for a reverse transcription reaction are mixed at room temperature, a non-specific reverse transcription reaction is caused by non-specific priming under this condition. Even at room temperature, non-specific priming occurs due to the high activity of reverse transcriptase to produce a number of unspecific cDNAs, and thus it is a major factor that increases non-specific amplification reactions. Due to such non-specific reverse transcription reactions, primers required for subsequent PCR reactions and limited concentrations of other essential components are consumed, and for this reason, the non-specific reverse transcription reactions act as competitive inhibitors. Non-specific reverse chain reactions are problematic when detecting a low concentration of RNA, and particularly, interfere with detection of a target RNA that is present in a very small amount in a solution that contains large amounts of RNAs extracted from cells or body fluids and having a high nucleotide sequence complexity. Thus, non-specific reverse transcription reactions make it difficult to detect a virus or gene present at a low concentration. Also, in multiplex reverse transcription reactions that are performed using various primers at the same time, non-specific reverse transcription reactions reduce specificity, making multiple detections difficult. This non-specific amplification is more greatly influenced by the relative amounts of the target nucleic acid and other nucleic acids derived from a biological sample than the absolute amount of the target nucleic acid. This is because non-specific hybridization of primers increases to increase non-specific reactions, when many RNAs other than a desired target are present in a reaction mixture.

In order to reduce such undesirable non-specific reactions and amplification, various attempts have been made. Specifically, there was an attempt to increase the detection limit of a specific target by more strongly hybridizing primers to the target. For example, a method was reported, in which the 5' terminus of primers are substituted with LNA so that it can more strongly hybridize to the target, thereby reducing non-specific amplification (Malgoyre A. et al., *Biochem Biophys Res Commun.* Mar. 2, 2007; 354(1):246-52). As another method for solving problems using a specific primer structure, a method of preventing primer dimer formation was also developed. When a reverse transcription reaction is performed particularly at low temperatures, polymerization can proceed by partial hybridization between primers to form a dimer, an important factor that rapidly reduces sensitivity in the reverse transcription reaction. In order to solve this problem, it was proposed to use primers formed by extending complementary nucleotide sequences so that five nucleotides of the 5' nucleotide sequence of the primers can form a hairpin structure at low temperature (Ji Young Hong et al., *Virol J.* 2011; 8: 330. Published online 2011; Korean Patent No. 10-0987352). However, this lock primer method has disadvantages in that, because the primers have high hybridization temperature due to the nucleotide sequence added to the 5' terminus, non-specific hybridization of the primers to non-specific targets having nucleotide sequences similar thereto in a subsequent PCR reaction can be induced, and the efficiency of hybridization in the hybridization step is reduced due to the hairpin structure of the primers.

To solve such problems, a method was developed which uses blocked primers that are partially complementary to primers and that are blocked at the 3' terminus. Such blocked primers have advantages in that, because they are blocked at the 3' terminus, they do not act as primers in a nucleic acid polymerization reaction, and because they are short in length, they hybridize to primers only at room temperature to prevent primer dimer formation, and because they are detached immediately from the primers and are not operated when the temperature increases in a subsequent reaction, instant reverse transcription PCR can be performed (Korean Patent Application No. 10-2011-0017226).

In addition, a method of performing a reverse transcription reaction at high temperature for more specific hybridization to a target RNA was developed. It was reported that, when a cDNA is synthesized at high temperature such as 70° C. using primers that hybridize at high temperature and a reverse transcription polymerase that operates even at high temperature, it can be more specifically amplified (Fuchs B, et al., *Mol Biotechnol,* 1999 October; 12(3):237-40).

In multiplex reverse transcription PCRs, specificity is more important. This is because several primers are used in the reaction, a non-specific reaction can occur in a subsequent PCR reaction due to a non-specific reaction in the reverse transcription reaction step. To avoid this non-specific reaction in multiplex reverse transcription PCRs, a reverse transcription reaction is first performed, and then a PCR reaction is performed, so that a more specific reaction can be achieved. However, in this case, the process of opening a reaction tube and adding a reaction solution to the open reaction tube is troublesome, and the possibility of contamination in the process of opening and operating the reaction tube is higher. For this reason, it is generally preferable to sequentially perform a reverse transcription reaction and PCR in a single tube. Thus, a method of physically separating reactions from each other while performing reverse transcription PCR in a single tube without opening the tube was developed, in which the reverse transcription reaction mixture is present at the bottom of the tube during the reaction, and the PCR reaction mixture is suspended from the cover. In this method, the reverse transcription reaction is performed in the tube while the PCR reaction mixture is suspended from the cover and is not reacted, and after completion of the reverse transcription reaction, and the reaction tube is rotated in a centrifuge so that the PCR solution suspended from the cover of the reaction tube is mixed with the reverse transcription reaction product, after which the PCR reaction is performed (Rodney Mark Ratcliff, et al., 2002 November; 40(11): 40914099. doi: 10.1128/JCM.40.11.4091-4099.2002).

As a result of efforts to solve the above-described problems occurring in conventional reverse transcription reactions, a "hot-start reverse transcription reaction" was developed. The hot-start reverse transcription reaction is a method for detecting a very small amount of a target RNA, in which a reverse transcription reaction can be initiated at a high temperature at which priming could occur only to an RNA having a nucleotide sequence exactly complementary to primers, thereby preventing non-specific priming from occurring at room temperature and preventing non-specific primer oligomerization, thereby increasing the specificity of the reverse transcription reaction. To implement this method, a method that uses a heat-resistant polymerase and an aptamer was developed and is being used. A light cycler RNA master kit (Roche) is a method employing Tth DNA polymerase and an aptamer. Tth DNA polymerase combines a function of polymerizing DNA using RNA as a template and a function of polymerizing DNA using DNA as a template. The aptamer used herein is attached to the reactive site of Tth DNA polymerase, and thus is inactive at room temperature. When the temperature of the reaction solution is increased to high temperature, the three-dimensional structure of the aptamer is modified so that it is separated from Tth DNA polymerase so as to be active, and the reverse transcription reaction of a specifically primed target RNA can be performed, and afterwards PCR can be performed. In addition, the GeneAmp AccuRT Hot Start RNA PCR kit (Applied Biosystems) uses a heat-resistant polymerase derived from *Thermus* specie Z05 and can perform a reverse transcription reaction and PCR by using a single enzyme, like the Tth DNA polymerase. Also, the reaction is performed using an aptamer specific thereto. Such products can reduce non-specific amplification in reverse transcription PCR by inhibiting enzymatic activity at room temperature using the aptamer to reduce non-specific reverse transcription reactions. However, when the temperature of the aptamer is increased to high temperature, the three-dimensional structure thereof is modified, but when the temperature is lowered, the aptamer is restored to its original structure to inhibit DNA polymerases. In other words, the aptamer has the problem of reversibly inhibiting DNA polymerases. For the GeneAmp AccuRT Hot Start RNA PCR kit, it is described that the aptamer is still attached to DNA polymerase even at 55° C. and is completely detached when the temperature becomes 65° C. Thus, in reactions in which the annealing temperature of primers that are generally used is 55° C. or below, there is a problem in that the activity of DNA polymerase is inhibited to reduce PCR efficiency. For this reason, a heat-resistant DNA polymerase such as Tth DNA polymerase, which has reverse transcription function, is used. This heat-resistant DNA polymerase has a problem in that, because it has reverse transcription function during a subsequent PCR process in which enzymatic activity is maintained, it causes a continuous non-specific reverse transcription reaction, resulting in non-specific amplification.

A hot-start PCR reaction method employing antibodies is applicable only to Taq DNA polymerase (Enneth, G. et al., 1994, *Biotechnology*, 12; 506-509). In order to perform hot-start reverse transcription reactions using other kinds of reverse transcription polymerases, a heat-resistant reverse transcriptase that is resistant at high temperature should be used, and for reverse transcription PCR, a reverse transcriptase-specific antibody that is detached at low temperature and a DNA polymerase-specific antibody that is detached at high temperature are required. For this reason, antibodies specific to the respective heat-resistant polymerases should be developed, and thus there is a technical limit to such hot-start reverse transcription reactions.

The present inventors developed a hot-start PCR method that uses pyrophosphate (PPi) and heat-resistant pyrophosphatase (PPase) (Korean Patent No. 10-0292883). This method is based on the principle in which PPi that strongly binds to magnesium ions essential for DNA polymerization is added to inhibit a polymerase reaction at room temperature, and then PPase is reacted at high temperature to remove PPi. Reverse transcriptase cannot be used in a hot-start method that uses an antibody, because of its low activation temperature. A conventional hot-start PCR method that uses an antibody is a method in which the activity of enzyme is inhibited by enzyme-antibody binding at low temperature, and the antibody loses its binding with the enzyme due to a decrease in its stability when it reaches high temperature, whereby a PCR reaction occurs. Reverse transcriptase has no thermal stability at high temperature, unlike DNA polymerase. When the antibody reaches high temperature to lose its binding with reverse transcriptase, the activity of reverse transcriptase is inhibited. In an attempt to solve this problem, a hot-start reverse transcription reaction method that uses PPi and PPase has advantages in that it can be generally applied regardless of the kind of DNA polymerase and in that reactivity can be continuously maintained by continuously removing PPi generated from dNTP during PCR. However, if a hot-start PCR master mix solution is made using this method, PPase will slowly dissolve PPi from $Mg^{2+}$ ions so that the activity of DNA polymerase will appear, and ultimately, a desired hot-start PCR reaction effect will be lost. In addition, if a reverse transcription reaction master mix solution containing PPase is made, it has a problem in that the activity of PPase at room temperature or 4° C. is maintained only for a short period of time, because PPase is very unstable. Thus, a mixture in a dried form having increased stability was developed (Korean Patent No. 10-1098764). Accordingly, in order to solve the above-described problems of hot-start reverse transcription reactions, technology for more highly sensitive hot-start reverse transcription and reverse transcription PCR is required.

DISCLOSURE OF INVENTION

It is an object of the present invention to provide a composition for hot-start reverse transcription reaction or hot-start reverse transcription PCR, which comprises pyrophosphate (PPi) and pyrophosphatase (PPase).

To achieve the above object, the present invention provides a composition for hot-start reverse transcription reaction, which comprises an $Mg^{2+}$ ion, four kinds of dNTPs, reverse transcription polymerase, pyrophosphate (PPi), and pyrophosphatase (PPase).

The present invention also provides a composition for hot-start reverse transcription PCR, which comprises an $Mg^{2+}$ ion, four kinds of dNTPs, reverse transcription polymerase, pyrophosphate (PPi), and pyrophosphatase (PPase), and further comprises DNA polymerase.

The present invention also provides a method of preparing a composition for a hot-start reverse transcription reaction, the method comprising introducing the above-described composition for the hot-start reverse transcription reaction into a single reaction tube.

The present invention also provides a kit for hot-start reverse transcription reaction, which comprises the above-described composition for hot-start reverse transcription reaction.

The present invention also provides a method for amplifying nucleic acid, the method comprising the steps of: mixing the above-described composition for hot-start reverse transcription PCR with a sample containing template RNA to obtain a reaction mixture; performing a reaction so as to amplify the reaction mixture to thereby obtain an amplification product; and analyzing the amplification product.

Lanes 1, 2, 3, 4, 5 and 6: products obtained from template hepatitis C virus RNAs having copy numbers of $10^6$, $10^5$, $10^4$, $10^3$, $10^2$ and 10;
A: the results obtained using a reaction solution having no hot-start reverse transcription function;
B: the results obtained from adding 1 μg of total RNA of human cell to the reaction solution of "A";
C: the results obtained using a hot-start reverse transcription reaction solution comprising PPi and PPase; and
D: the results obtained from adding 1 μg of total RNA of human cell to the reaction solution of "C".

Figure 6A:
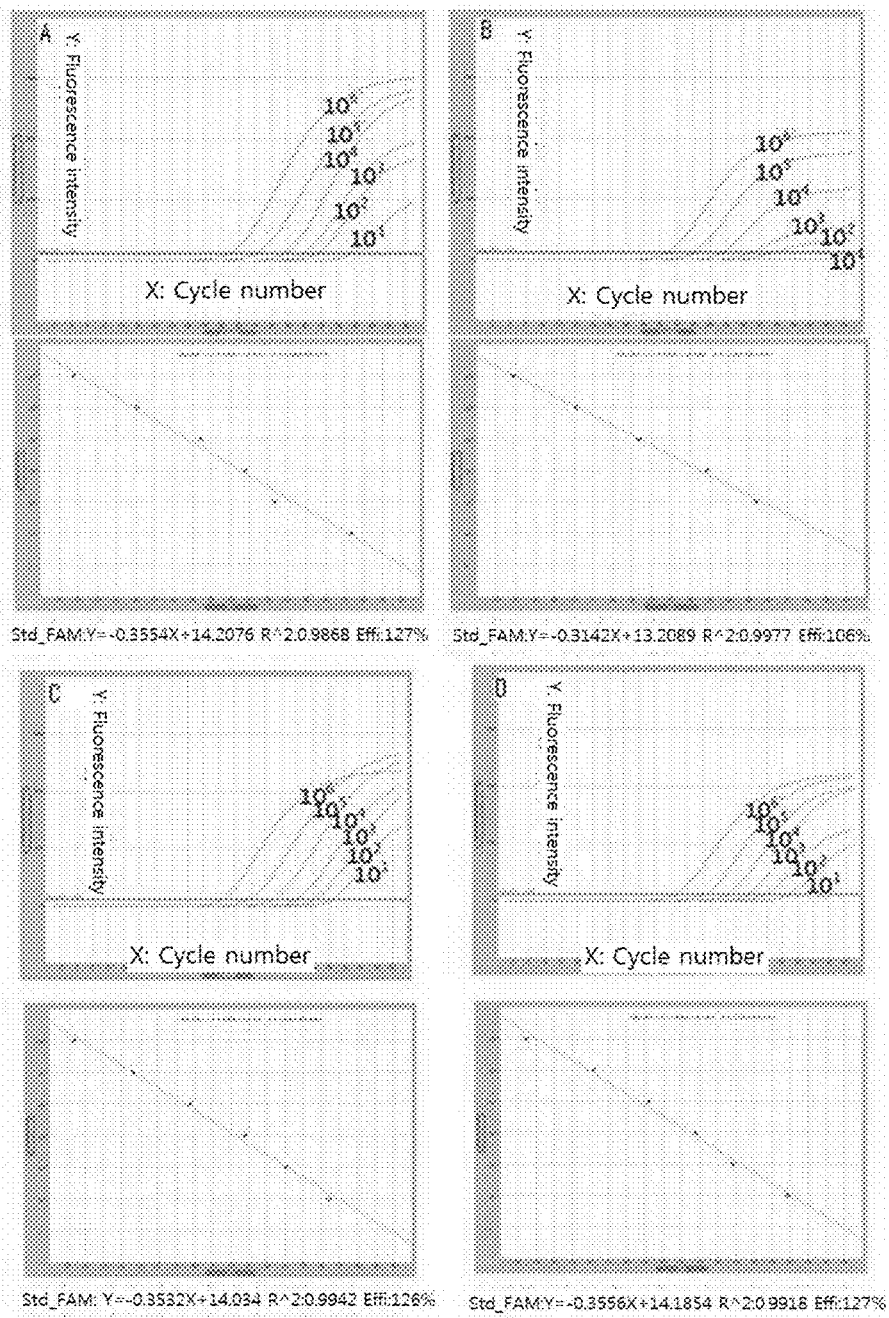
Figure 6B:
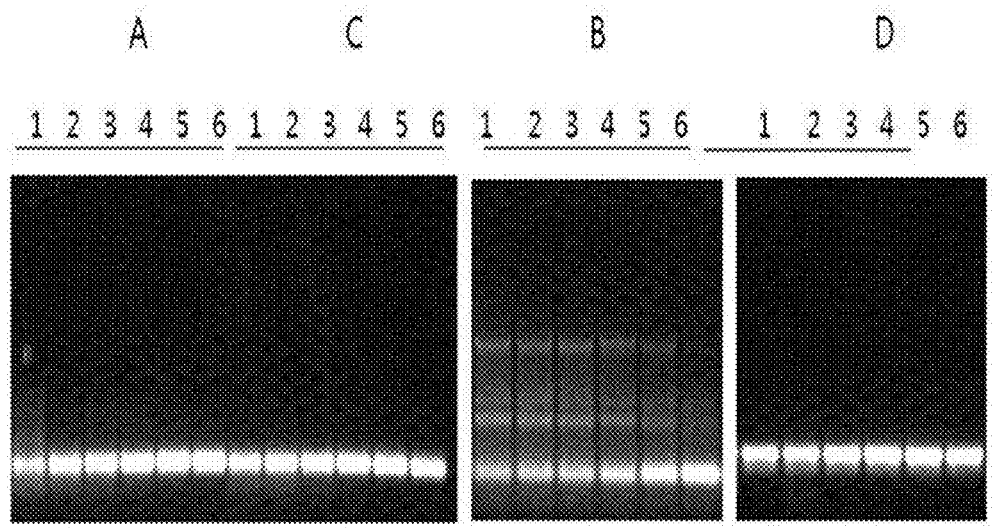
Figure 7A:
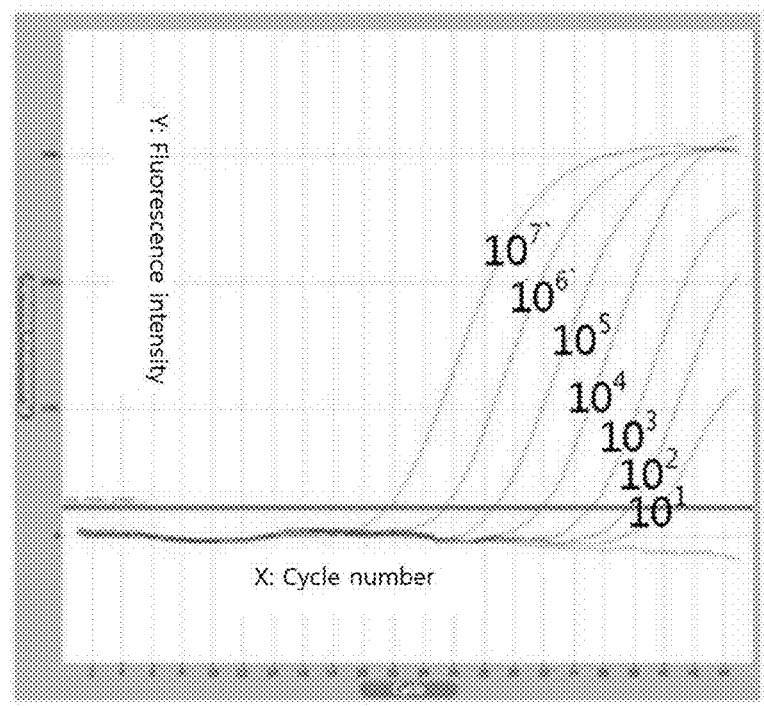
Figure 7B:
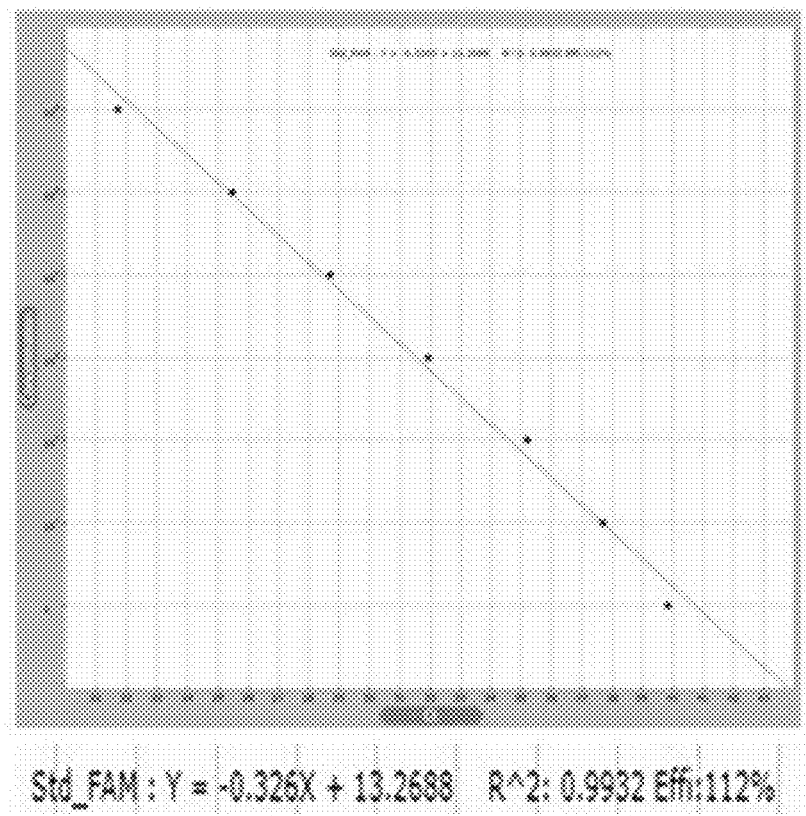
Figure 7C:
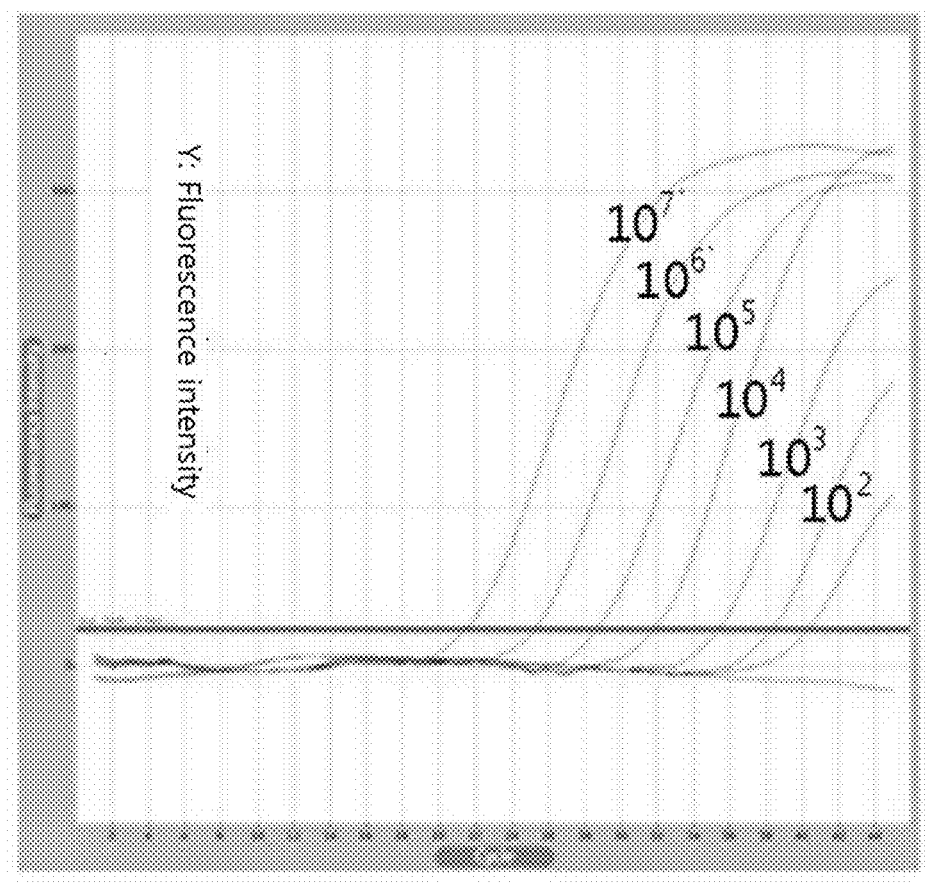

FIG. 6a shows a comparison of the inhibition of non-specific reactions in real-time reverse transcription PCR between the use of hot-start reverse transcription reaction solution and Taq antibody:
A: the results obtained using a reaction solution having no hot-start reverse transcription function, which comprises Taq antibody, together with a hot-start PCR reaction solution;
B: the results obtained from adding 1 μg of total RNA of human cell to the reaction solution of "A";
C: the results obtained using a hot-start reverse transcription reaction solution, which comprises PPi and PPase, together with a hot-start PCR reaction solution; and
D: the results obtained from adding 1 μg of total RNA of human cell to the reaction solution of "C";

FIG. 6b shows the results of electrophoresis of real-time reverse transcription PCR products on 2% agarose gel:
Lanes 1, 2, 3, 4, 5 and 6: products obtained from template hepatitis C virus RNAs having copy numbers of $10^6$, $10^5$, $10^4$, $10^3$, $10^2$ and 10;
A: the results obtained using a reaction solution having no hot-start reverse transcription function, which comprises Taq antibody, together with a hot-start PCR reaction solution;
B: the results obtained from adding 1 μg of total RNA of human cell to the reaction solution of "A";
C: the results obtained using a hot-start reverse transcription reaction solution, which comprises PPi and PPase, together with a hot-start PCR reaction solution;
D: the results obtained from adding 1 μg of total RNA of human cell to the reaction solution of "C";

FIGS. 7a and 7c are the graphs of real-time reverse transcription PCR, which illustrate that a solution-state reverse transcription/PCR composition and a dry-state reverse transcription/PCR composition exhibit equal performance in real-time reverse transcription PCR (FIG. 7a: solid state; FIG. 7c: dry state).

Figure 7D:
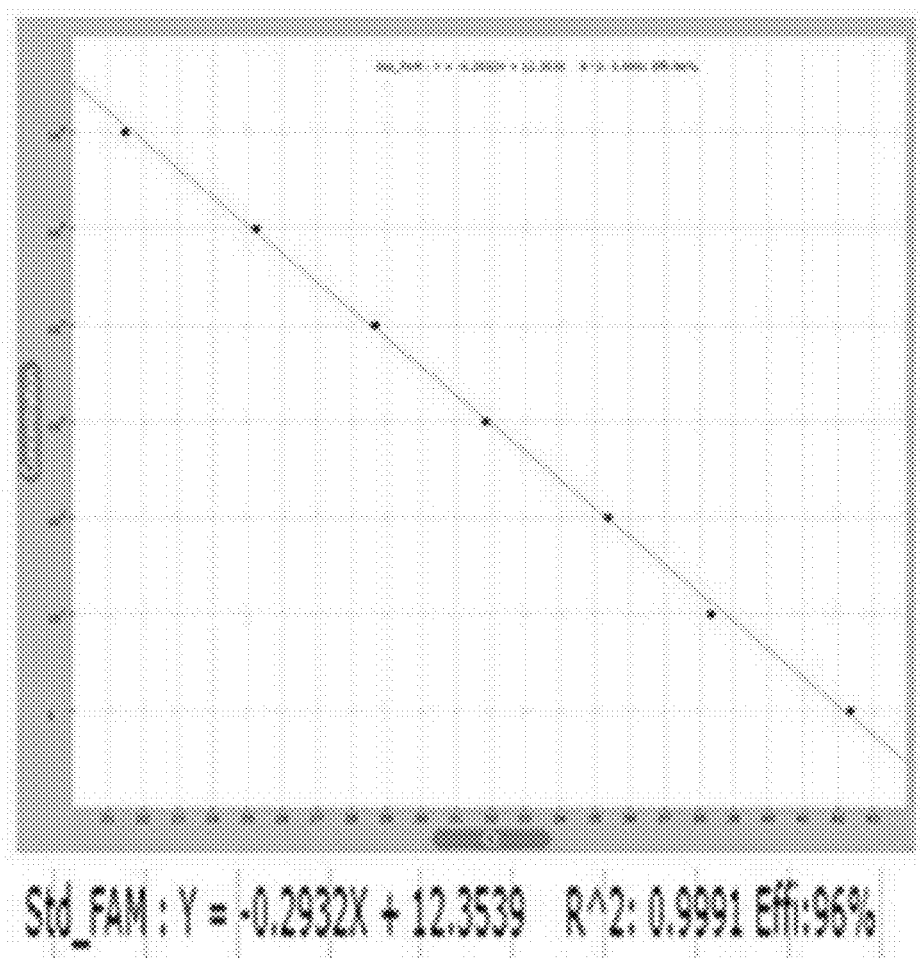

FIGS. 7b and 7d are the standard graphs of real-time reverse transcription PCR, which illustrate that a solution-state reverse transcription/PCR composition and a dry-state reverse transcription/PCR composition exhibit equal performance in real-time reverse transcription PCR (FIG. 7b: solid state; FIG. 7d: dry state).

Figure 8A:
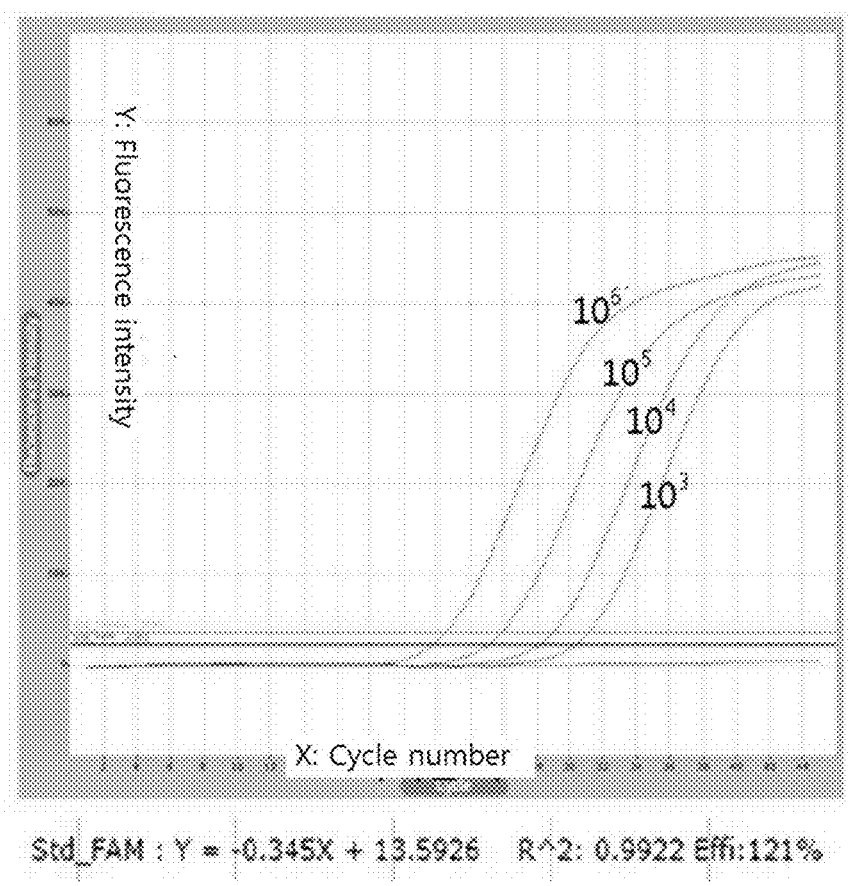

FIG. 8a is a graphic diagram showing the results of performing real-time reverse transcription PCR using a liquid-state mixture as a control in order to test the stability of a dry reverse transcription/PCR composition as a function of storage period.

Figure 8B:
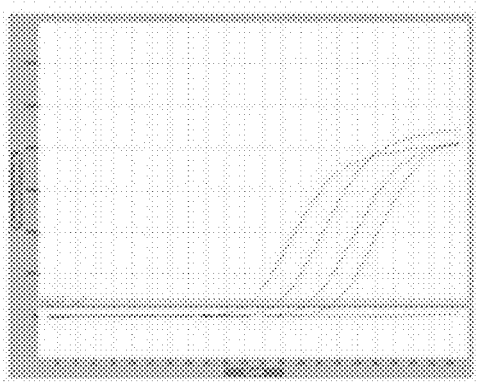
Figure 8B:
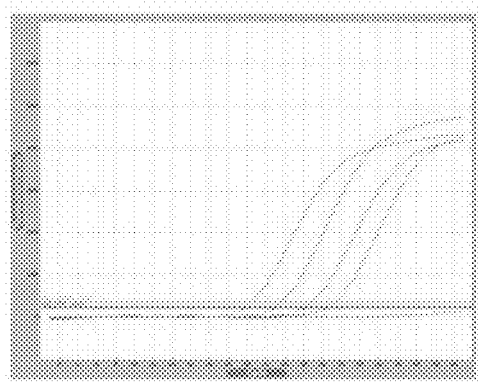
Figure 8B:
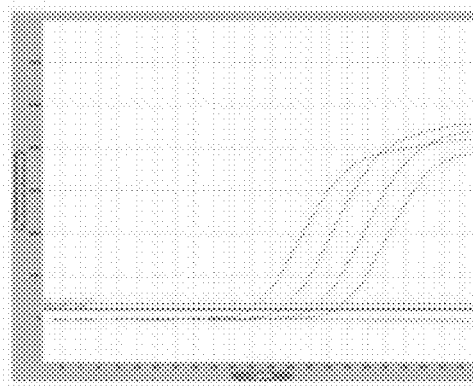
Figure 8B:
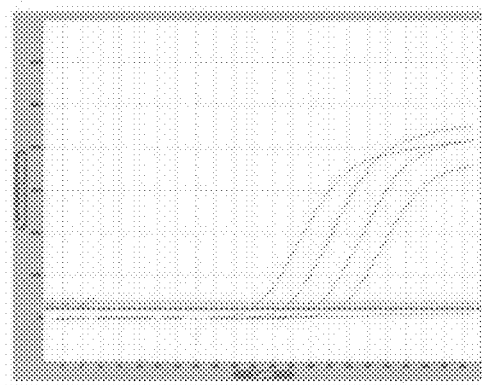
Figure 8B:
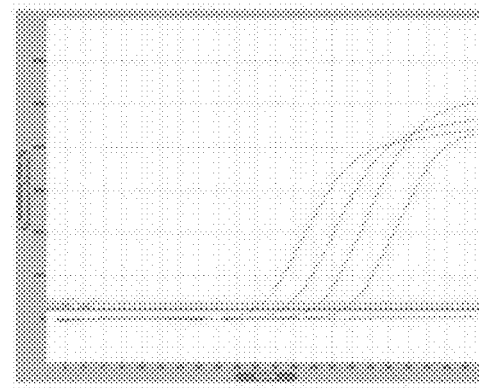

FIG. 8b is a graphic diagram showing the results of performing real-time reverse transcription PCR using a dry mixture at one-day intervals for a storage period of a total of 5 days after storage at 50° C. in order to test the storage stability of the dry mixture:
1 day to 5 days: the number of days during which the dry mixture was stored at 50° C.

Figure 9A:
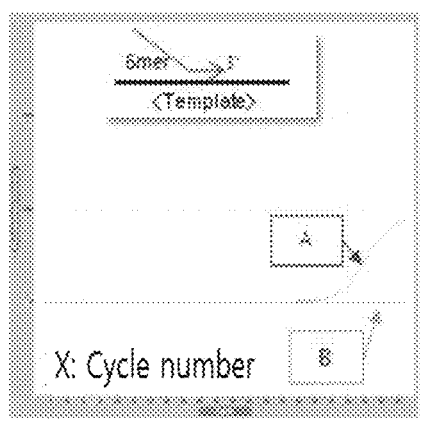
Figure 9B:
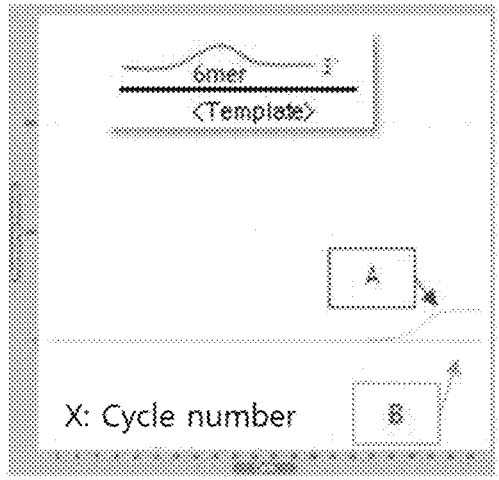

FIG. 9a shows the results of performing real-time reverse transcription PCR using a primer having 6 mismatch nucleotides at the 5' end, and FIG. 9b shows the results of performing real-time reverse transcription PCR using a primer having 6 mismatch nucleotides at the middle. Also, FIGS. 9a and 9b graphically show the results of performing real-time reverse transcription to confirm the inhibition of non-specific binding of a primer to a template in a hot-start reverse transcription PCR reaction mixture.

Figure 10A:
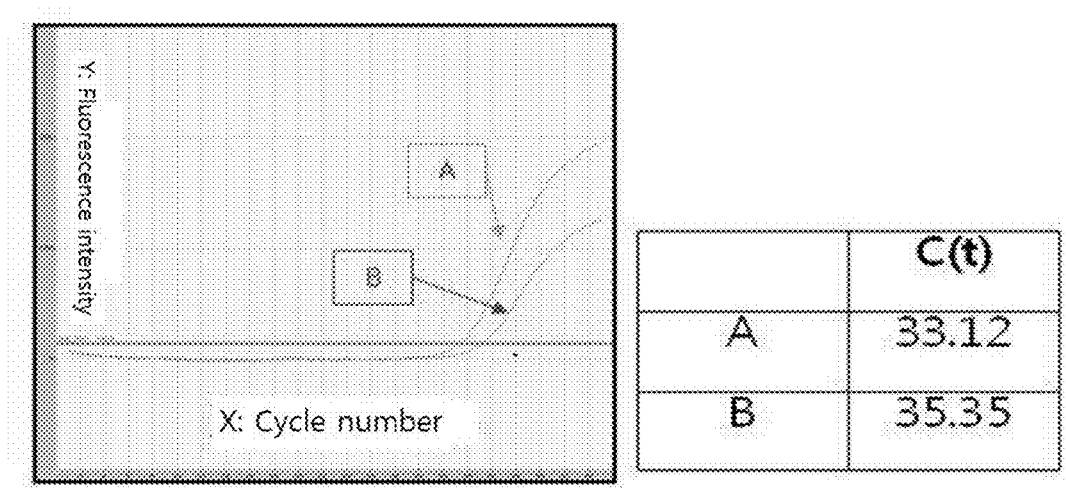
Figure 10B:
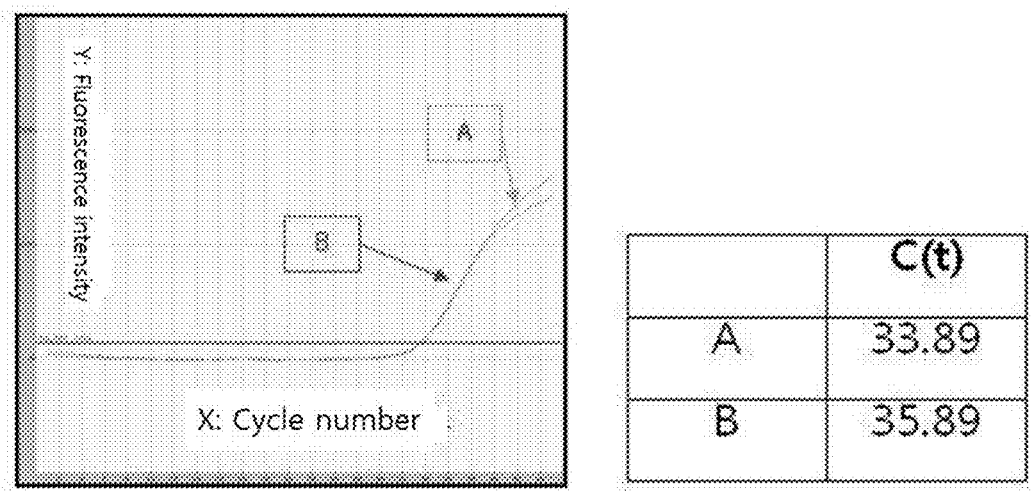

FIGS. 10a and 10b are graphs showing the results of performing real-time reverse transcription PCR in order to analyze the single nucleotide polymorphism of RNA by hot-start reverse transcription PCR:

"A" indicates the result obtained using a primer having an exactly matched nucleotide sequence, and "B" indicates the result obtained using a primer having a single mismatch nucleotide.

Figure 11:
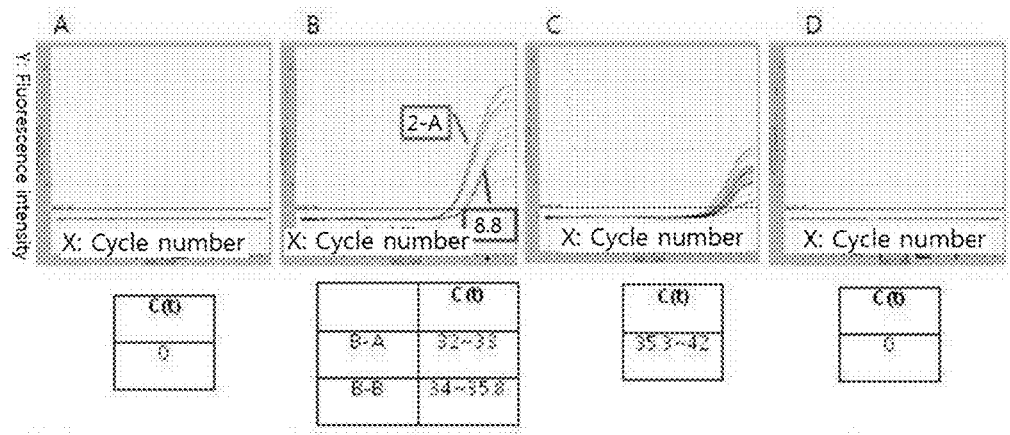

FIG. 11 graphically showing the results of performing real-time reverse transcription in order to examine whether a hot-start reverse transcription reaction inhibits non-specific reactions resulting from RNA-RNA self-priming:

"A" in FIG. 11 shows the results of performing a real-time PCR using RNA alone without a reverse transcription reaction; and "B" shows the results of performing a reverse transcription reaction using a primer, followed by real-time PCR. "B-A" indicates the result obtained by performing the reverse transcription reaction using a hot-start reverse transcription reaction solution, and "B-B" shows the result obtained by performing the reverse transcription reaction using a reaction solution having no hot-start reverse transcription function. "C" shows the results of performing a reverse transcription reaction using RNA alone in a reaction solution having no hot-start reverse transcription function, followed by real-time PCR. "D" shows the results of performing a reverse transcription reaction using RNA alone in a hot-start reverse transcription reaction solution, followed by real-time PCR.

Figure 12:
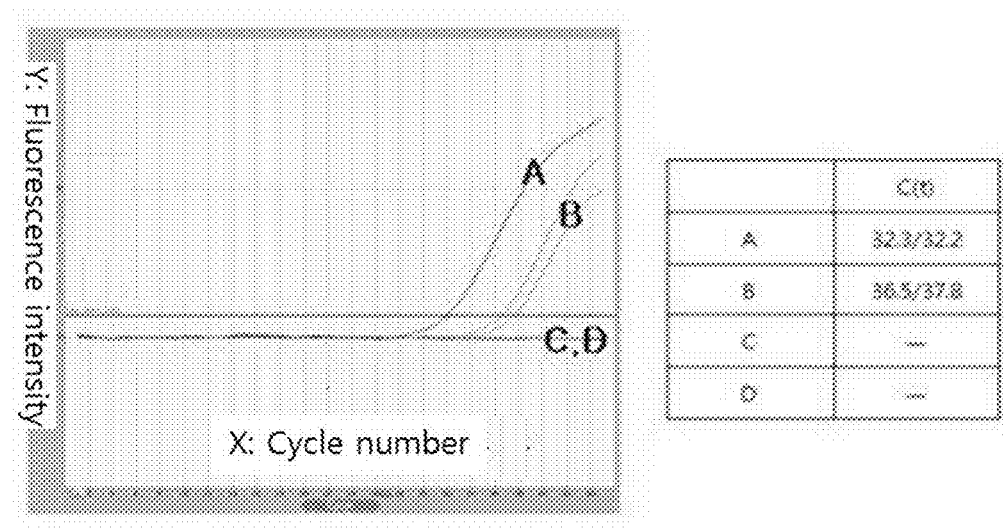

FIG. 12 is a graphic diagram showing the results of performing real-time reverse transcription PCR in order to examine whether RNA-RNA self-priming in a reverse transcription reaction is inhibited by RNA termination. "A" and "B" indicates the result obtained using non-terminated RNA, and "C" and "D" indicate the results obtained using terminated RNA. For "A" and "C", a plain reverse transcription reaction was performed, and for "B" and "D", a hot-start reverse transcription reaction was performed.

Figure 13A:
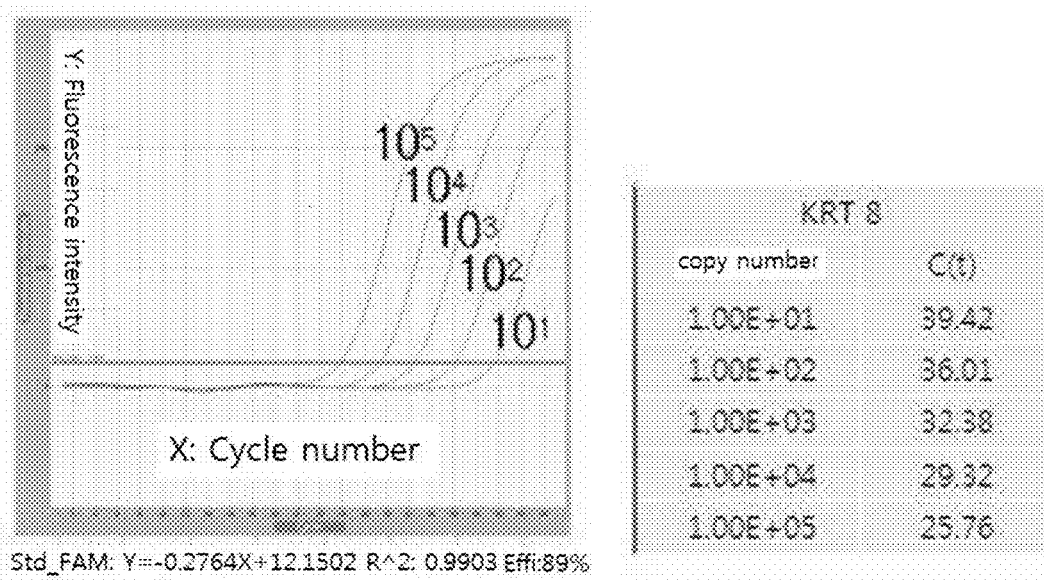

FIG. 13a shows the results of detecting the cancer marker keratin-8 using RNA extracted from Hela cells. For quantitative analysis, the extracted RNA was serially 10-fold diluted and was subjected to real-time reverse transcription PCR in order to plot a standard curve. FIGS. 13b, 13c, 13d and 13e are graphs showing the results of performing real-time reverse transcription PCR in order to examine whether RNA termination and hot-start reverse transcription PCR increase the detection limit of the cancer marker.

BEST MODE FOR CARRYING OUT THE INVENTION

In one aspect, the present invention is directed to a composition for hot-start reverse transcription reaction, which comprises an $Mg^{2+}$ ion, four kinds of dNTPs, reverse transcription polymerase, pyrophosphate (PPi), and pyrophosphatase (PPase).

The Reverse transcription polymerase that is used in the present invention may be any known reverse transcription polymerase. Specifically, commercially available AMV or MMLV may generally be used.

As pyrophosphatase (PPase), commercially available conventional PPase may be used in the present invention without limitation. Specifically, PPase that is used in the present invention may preferably be Tte-inorganic pyrophosphatase (SibEnzyme Ltd.) derived from an *E. coli* cloned with an inorganic pyrophosphatase gene derived from *Thermus thermophilus* B35, or Pto-inorganic pyrophosphatase (Bioneer corporation, Korea) derived from an *E. coli* cloned with an inorganic pyrophosphatase gene derived from *Picrophilus torridus*. 1 unit of Pto-inorganic pyrophosphatase is defined as the amount of the enzyme required to produce 40 nmole of phosphate from pyrophosphate for 1 minute. The reaction is performed using Tris-HCl (pH 7.5), 5 mM $MgCl_2$, and 2.0 mM PPi with a total reaction volume of 0.5 ml at 70° C. for 10 minutes.

PPi that is contained in the composition may be added at a concentration of 0.1-5.0 mM, preferably 0.2-3.0 mM, based on the final reaction solution. If the concentration of PPi is higher than 5.0 mM, the concentration of PPase to be used needs to increase proportionately, and in this case, the amount of the reverse transcription reaction product can decrease. If the concentration of PPi is lower than 0.1 mM, the ability to capture the $Mg^{2+}$ ion in the reverse transcription reaction composition will be reduced, and thus the effect of inhibiting the production of non-specific products caused by non-specific priming (mispriming) cannot be obtained. When the concentration of PPi is 0.1-5 mM, 0.005-0.25 U of PPase is preferably contained in the reverse transcription reaction mixture. PPase is used 0.005-0.25 U per 0.1 mM PPi. If PPase is used at a concentration higher than 0.25 U per 0.1 mM PPi, the result can be confirmed at a higher concentration when a high-copy-number template is used, compared to when a low-copy-number template is used, and the reverse transcription reactivity can be reduced, resulting in a significant decrease in the amount of the reaction product. If the concentration of PPase is lower than 0.005 U per 0.1 mM PPi, the reverse transcription reaction can be inhibited.

The reaction buffer solution that is used in the present invention is preferably a buffer (pH 9.0) containing 10 mM Tris HCl and 40 mM KCl, and the four kinds of dNTPs indicate dATP, dTTP, dGTP and dCTP. If necessary, the composition may further comprise substances required for reverse transcription reaction, including primers, template nucleic acid and the like. The primers may preferably be random primers, or primers specific for the template nucleic acid, and the template nucleic acid is preferably an RNA in need of a reverse transcription reaction. Additionally, the composition may comprise a fluorescent dye that may be selected from the group consisting of SyBr Green, EtBr and HRdye.

The composition for reverse transcription reaction according to the present invention may further comprise reverse transcription primers. The reverse transcription primers that are used in the present invention may be any primers that can anneal the template RNA to perform the reverse transcription of the RNA. Specifically, the reverse transcription primers may be poly A primers, or primers specific to the template RNA.

Meanwhile, the composition for reverse transcription reaction according to the present invention may comprise a dye and/or a polyol, which is not reactive with nucleic acid, for the purposes for the convenience of experiments, the prevention of contamination by PCR products, the stabilization of DNA polymerase and dNTPs and the improvement of reactivity.

The "non-reactive dye" should be selected from among substances that do not influence reverse transcription reactions, and it is used to analyze or identify PCR reactions using reverse reaction products. Examples of substances that satisfy such conditions include water soluble dye such as rhodamine, tamra, lax, bromophenol blue, xylene cyanole, bromocresol red, and cresol red. Among them, xylene cyanole is preferably used. The non-reactive dye may be contained in an amount of 0.0001-0.01 wt %, preferably 0.001-0.005 wt %, and more preferably 0.001-0.003 wt %, based on the total weight of the composition. If the content of the non-reactive dye in the composition is less than 0.0001 wt %, it will be difficult to visually observe the migration of a sample during agarose gel electrophoresis for analysis after the reverse transcription reaction, because the concentration of the dye is low. If the content of the non-reactive dye in the composition is higher than 0.01 wt %, a high concentration of the water-soluble dye can act as a reaction inhibitor during the reverse transcription reaction. In addition, this dye can interfere with the migration of the sample during agarose gel electrophoresis.

Also, the polyol can be used as an additional stabilizer for further stabilizing the composition of the present invention, and may be one or more compounds selected from the group consisting of glucose, glycerol, mannitol, galacitol, glucitol, and sorbitol. The content of the polyol in the composition may be 10-500 mM, and preferably 50-300 mM. If the content of the polyol is higher than 500 mM, it will be difficult to dissolve with an aqueous solution, due to the solubility of the water-soluble polymer itself, will be difficult to mix sufficiently, due to its high viscosity, will increase the volume of the composition to a volume greater than required, and will not be easily dissolved in a sterile distilled water and gene solution before the reverse transcription reaction. In addition, a high-concentration of the water-soluble polymer can act as a reaction inhibitor during the reverse transcription reaction. On the other hand, if the content of the polyol in the composition is less than 10 mM, the target enzyme and surface water molecules cannot be sufficiently coated so that they cannot be protected, and thus the effect of efficiently stabilizing the enzyme cannot be obtained. In addition, the solution can spread throughout the bottom of the tube due to its too low viscosity and cannot be dried in an ideal form, and the enzyme cannot be sufficiently protected. In the present invention, in addition to the polyol, gelatin, bovine serum albumin, Thesit or PEG-8000 may be used as a stabilizer.

The composition of the present invention is preferably freeze-dried or dried in order to increase the stability, the convenience of storage and the long-term storage stability thereof. The drying may be performed by a known drying method, such as room temperature drying, drying at elevated temperature, for example, 40 to 60° C., freeze drying, or reduced pressure drying. In addition, any drying method may be used, as long as the component of the composition is not lost. The drying method as described above may be applied depending on the kind and amount of enzyme used. In the present invention, the freezing drying method or the reduced pressure method employing vacuum centrifugation may preferably be used.

The composition for hot-start reverse transcription PCR may be prepared in a stable form by introducing the reaction mixture into a single reaction tube, and then immediately, freezing or drying the reaction mixture.

If necessary, the reaction mixture may further comprise a primer, a probe, template nucleic acid, a fluorescent dye, a non-reactive dye and/or a polyol.

As the DNA polymerase, any known DNA polymerase may be used in the present invention without particular limitation. Among these polymerases, a polymerase having 5'→3' exonuclease activity, a polymerase having 3'→5' exonuclease activity, and a polymerase that does not have 5'→3' exonuclease activity and 3'→5' exonuclease activity may be used alone or in combination. Examples of the polymerase having 5'→3' exonuclease activity include Taq DNA polymerase, examples of the polymerase having 3'→5' exonuclease activity include Pfu DNA polymerase or TLA DNA polymerase (Bioneer), and examples of the polymerase having no 5'→3' exonuclease activity and 3'→5' exonuclease activity include Top DNA polymerase (Bioneer). The DNA polymerase may be contained in the composition for reverse transcription PCR at a concentration of 0.1-10 U (unit), preferably 0.5-2 U, and most preferably 1 U. The Taq, Pfu, Top and TLA DNA polymerases have the characteristics shown in Table 1 below.

TABLE 1

|  | Taq. DNA polymerase | Pfu DNA polymerase | Top DNA polymerase | TLA DNA polymerase |
| --- | --- | --- | --- | --- |
| 5'->3' exonuclease activity | Yes | No | No | No |
| 3'->5' exonuclease activity | No | Yes | No | Yes |
| End transferase activity | Yes | No | Yes | No |
| Error rate (×10⁻⁶) | 4.91 | 1.90 | unconfirmed | unconfirmed |
| Size of segments | ≤10 kbp | ≤5 kbp | ≤10 kbp | ≤15 kbp |
| Optimum activity temperature (° C.) | 72 | 72 | 72 | 72 |
| Half life (min, at 95° C.) | 80 | unconfirmed | unconfirmed | unconfirmed |
| MgCl$_2$ (mM) | 1.5 | — | 1.5 | 1.0 |
| MgSO$_4$ (mM) | — | 2.0 | — | — |
| KCl (mM) | 40 | 10 | 30 | 70 |
| optimum pH (at 25° C.) | 9.0 | 8.8 | 9.0 | 9.0 |

In addition, the composition for reverse transcription PCR may be used in, in addition to reverse transcription PCR, any nucleic acid amplification reaction such as multiplex reverse transcription PCRs, real-time reverse transcription PCR, real-time quantitative PCR or multiple real-time reverse transcription PCRs.

In the present invention, the composition for reverse transcription PCR may further comprise a substance that shows a hot-start PCR effect by binding to DNA polymerase or regulating the action of DNA polymerase. This substance may be selected from the group consisting of an antibody, an aptamer and an affibody, which bind to DNA polymerase.

In the present invention, the DNA polymerase may be in a modified form and may have a hot-start PCR effect, and examples of this enzyme include, but are not limited to, Tth polymerase.

PPase is preferably a heat-stable enzyme that is thermally stable even at a temperature of 70° C. or above. It is thermally stable during the reverse transcription and PCR processes. Particularly, PPase shows enzymatic activity at a temperature similar to the temperature at which reverse transcriptase and DNA polymerase react. For this reason, reverse transcription reaction and PCR are prevented from occurring during the mixing process and PPase is reacted to decompose PPi at a temperature equal to or higher than the temperature at which primers specifically hybridize, whereby reverse transcriptase can be activated while reverse transcription reaction can be initiated at the hybridization temperature of the primers, to eliminate non-specific cDNA synthesis. In addition, when the DNA polymerase hybridizes, non-specific nucleic acid amplification can be prevented. As a result, selectivity can be greatly increased compared to that of conventional reverse transcription/PCR, and a very small amount of the target nucleic acid can be successfully detected. Thus, the inventive composition for hot-start reverse transcription reaction or reverse transcription PCR comprising PPi and PPase is a stable composition that can solve problems of non-specific reverse transcription reaction occurring in conventional reverse transcription reaction, and the resulting non-specific PCR amplification, and that can specifically amplify a desired target product without troublesomeness to provide an accurate amplification result.

Specifically, the composition for hot-start reverse transcription reaction according to the present invention has the following advantages over various reverse transcription reaction compositions that have been reported in the prior art and have been commercially used:

1) Even when a target RNA is contained in a very small amount in the total RNA of a reaction solution, the composition for hot-start reverse transcription PCR according to the present invention can selectively perform the reverse transcription of the target RNA to perform PCR amplification in a manner specific to the target RNA. Thus, the composition of the present invention it makes it possible to detect a very small amount of RNA virus or analyze a cancer-related RNA gene.

2) The composition of the present invention can prevent the production of amplification products caused by non-specific priming, and thus can simultaneously detect various targets in multiplex reverse transcription PCRs in which reverse transcription PCR reactions for various targets are simultaneously performed.

3) Because all the components of the reaction mixture for reverse transcription PCR, which are used in the present invention, are prepared as a single mixture, a separate mixing process is not required during reverse transcription PCR, and thus the occurrence of error caused by mixing during the reaction can be prevented. In addition, the occurrence of non-specific PCR products can be prevented, the experiment can be conveniently performed, contamination by reverse transcription PCR reaction products can be prevented, and the stability and reactivity of reverse transcription polymerase, DNA polymerase and dNTPs can be increased.

4) When nucleic acid is used in a mixture with a stabilizer, stability is increased, it is easy to use and convenient to store.

In a preferred embodiment of the present invention, in order to solve the problems of non-specific reverse transcription reactions occurring in the prior art and perform hot-start reverse transcription reaction in a target-specific manner, only a desired RNA into cDNA is synthesized and PPi and PPase were used in the reverse transcription reaction to perform a PCR reaction in a manner specific to the synthesized cDNA to thereby amplify a desired RNA with high sensitivity. Specifically, 0.5 mM to 2.0 mM (preferably 2.0 mM) of PPi and 0.005 U to 0.25 U, preferably 0.1 U of PPase were added to a reverse transcription reaction mixture containing reverse transcription polymerase, and then a reverse transcription reaction was performed using the reaction mixture at 42° C. for 60 minutes. As a result, it was shown that, when no PPase was added, reverse transcription reactions were inhibited by PPi (see FIG. 1), but PPi and PPase were added, reverse transcription and PCR reactions were activated to increase the amount of the reaction product (see FIGS. 2 and 3). In addition, it was shown that, when the gene of hepatitis C virus was amplified using PPi and PPase, a template RNA having a copy number of $10^{10}$ to 10 could be detected (see FIG. 4), and when the total RNA extracted from human cells, in addition to the template RNA of hepatitis C virus, was added, non-specific reactions caused by the human RNA were inhibited, and RNAs other than the target RNA did not result in a decrease in reaction efficiency and changes in sensitivity and detection ability. However, in the absence of PPi and PPase, non-specific reactions were caused by the added human RNA (see FIGS. 5a and 5b). Moreover, it was shown that, in the hot-start reverse transcription PCR method, non-specific reactions were significantly reduced compared to those in conventional hot-start PCR methods employing Taq antibody, and thus a target RNA with even a copy number of 10 was selectively detected with high sensitivity (see FIGS. 6a and 6b). In addition, the composition for hot-start reverse transcription PCR according to the present invention was dried to increase the stability and storage stability thereof, and it was found that the dried composition could stably show reactivity and amplification results similar to those of the composition that was not dried (see FIGS. 7 and 8).

Accordingly, the composition for hot-start reverse transcription reaction and the composition for reverse transcription PCR can be used to perform high-sensitivity reverse transcription reaction and PCR, and thus can be advantageously used in RNA amplification technologies for examination of various viruses and examination of cancer gene expression.

In the present invention, in order to prevent the template nucleic acid itself from being non-specifically self-primed and amplified in nucleic acid amplification reactions such as a PCR reaction or real-time quantitative PCR reaction for detecting the target nucleic acid, a method may additionally be used, in which a substance for terminating polymerization reaction and a nucleic acid polymerase are added to the template nucleic acid to perform a termination reaction so that the template nucleic acid cannot act as a primer, and thus only the target nucleic acid can be amplified and detected with high sensitivity.

Thus, the composition of the present invention can be characterized in that it further comprise a template nucleic acid that has a nucleic acid polymerization terminator bound to the 3' end to prevent non-specific nucleic acid polymerization. The nucleic acid polymerization terminator may be a nucleic acid-like compound that is activated in the form of triphosphate capable of acting on nucleic acid polymerase and has groups other than a hydroxyl group at the 3' end.

In the present invention, the template nucleic acid that has the nucleic acid polymerization terminator bound thereto to prevent non-specific nucleic acid polymerization is prepared by the following nucleic acid preparation method comprising the steps of: 1) terminating the 3' end of the template nucleic acid with a reaction mixture containing nucleic acid polymerase, enzymatic reaction buffer and a nucleic acid polymerization terminator; and 2) inactivating or removing the nucleic acid polymerization terminator from the reaction mixture.

More specifically, the nucleic acid preparation method may comprise the steps of: 1) separating and purifying nucleic acid from a biological sample containing the nucleic acid; 2) terminating the 3' end of the separated and purified template nucleic acid of step 1) with a reaction mixture containing nucleic acid polymerase, enzymatic reaction buffer and a nucleic acid polymerization terminator; and 3) inactivating or removing the nucleic acid polymerization terminator from the reaction mixture containing the nucleic acid terminated at the 3' end.

The nucleic acid preparation method described in the present invention may be performed using a known conventional nucleic acid extraction device, for example, a device described in Korean Patent No. 10-0148239, U.S. Pat. No. 5,702,590, U.S. Pat. No. 5,647,994, EP 0691541, U.S. Pat. No. 5,336,760, U.S. Pat. No. 5,897,783, U.S. Pat. No. 6,187,270, or Korean Patent Application No. 10-2008-0032904. In addition, ExiPrep™ 16-fully Automated DNA/RNA/Proteins Purification System (Bioneer, Korea) may preferably be used as an automatic nucleic acid extraction device in the present invention.

In the present invention, the sample may be a sample that contains nucleic acid (polynucleotide) and that is derived from any plant, animal, bacterium or virus.

In the present invention, the nucleic acid is RNA or DNA, and the nucleic acid polymerase comprises any nucleic acid polymerase that enables a terminator to be attached to the 3' end of DNA or RNA so as to terminate polymerization.

More specifically, the nucleic acid polymerase that is used in the present invention is preferably a polymerase that has no 3'→5' exonuclease activity so as not to hydrolyze the terminator. More preferably, it is a polymer that loses its enzymatic activity at a temperature of 90° C. or higher. The nucleic acid polymerase may comprise at least one selected from among RNA-dependent RNA-polymerase, RNA-dependent DNA-polymerase, DNA-polymerase, and RNA-polymerase.

As used herein, the term "nucleic acid polymerization terminator" refers to a substance that terminates the polymerization of all the fragments of the template nucleic acid so that the nucleic acid no longer elongates. It also refers to a substance that is bound to the end of the template nucleic acid fragment so that the chain elongation of the nucleic acid can no longer occur.

As used herein, the term "termination" means that the "nucleic acid polymerization terminator" is covalently bound to the 3' end of nucleic acid to terminate the polymerization of the nucleic acid, and the substance that is used for termination is defined as a terminator.

More specifically, the term "termination" as mentioned herein means that a substance having no hydroxyl group at 3' end or having a chemical group that terminates a polymerization reaction caused by polymerase is covalently bound to the 3' end of nucleic acid to terminate the polymerization of the nucleic acid, and the substance that is used for termination is defined as a terminator.

In the present invention, the nucleic acid terminator is a nucleic acid-like compound activated in the form of triphosphate capable of acting on nucleic acid polymerase and may be selected from among various nucleotide triphosphates that lack the 3' hydroxyl group to which nucleic acid is linked or which are substituted with other groups. It may be a nucleic acid terminator having good reactivity with nucleic acid polymerase.

The nucleic acid-like compound that can be used in the present invention may comprise at least one selected from among 2'3'-dideoxynucleoside 5'-triphosphate, 3'-deoxyadenosine 5'-triphosphate, 3'-azido-3'-deoxythymidine 5'-triphosphate, 1-β-d-Arabinofuranosylnucleoside 5'-Triphosphate, acyclo-guanosine triphosphate, 3'-amino-2'-deoxynucleoside 5'-triphosphate, and 3'-fluoro-3'-deoxynucleoside 5'-triphosphate.

More specifically, DNA-polymerase derived from *E. coli* or heat resistance bacteria may be 2'3'-dideoxynucleotide triphosphate (ddNTP) that has been frequently used in the dideoxy sequencing method developed by Sanger.

In the present invention, the dideoxynucleotide triphosphate (ddNTP) may comprise at least one selected from among dideoxyguanosine triphosphate (ddGTP), dideoxyadenosine triphosphate (ddATP), dideoxythymidine triphosphate (ddTTP), and dideoxycytidine triphosphate (ddNTP).

The deoxynucleotide triphosphate (dNTP) may comprise at least one selected from among guanosine, adenosine, thymidine, uridine and cytidine.

For example, various nucleic acid polymerization terminators may be used to perform a termination reaction using DNA-polymerase. When DNA-polymerase derived from mammalian is used, it is possible to use 5'-triphosphate 1-β-d-arabinofuranosylcytosine or 5'-triphosphate 9-β-d-arabinofuranosyladenine, which has high reactivity with this enzyme (Inhibition of Mammalian DNA Polymerase by the 5'-Triphosphate of 1-β-d-Arabinofuranosylcytosine and the 5'-Triphosphate of 9-β-d-Arabinofuranosyladenine, J. J. Furth, and Seymour S. Cohen, Cancer Res October 1968 28; 2061).

In addition, acyclonucleoside triphosphate that has frequently been used as an antiviral agent for inhibiting viral DNA-polymerases may also be used as the nucleic acid polymerization terminator (Inhibition of herpes simplex virus-induced DNA polymerase activity and viral DNA replication by 9-(2-hydroxyethoxymethyl)guanine and its triphosphate. P A Furman, M H St Clair, J A Fyfe, J L Rideout, P M Keller and G B Elion, J. Virol. October 1979 vol. 32 no. 172-77).

In addition, poly A polymerase that is RNA polymerase is an enzyme that is used to attach adenosine to the 3' end of RNA and is suitable for the nucleic acid polymerization termination as described in the present invention. When this enzyme is used, 3'-deoxyadenosine triphosphate (3'-dATP; cordycepin) known as an inhibitor of poly A polymerase may be used.

In the present invention, step 2) is a process of inactivating or removing unreacted nucleic acid polymerization terminator after step 1), in which inactivation of the nucleic acid polymerization terminator may be performed using any enzyme capable of hydrolyzing the triphosphate bond of various nucleic acid polymerization terminators that are used in polymerization.

More specifically, the nucleic acid terminator is preferably easily inactivated by heat, because it loses its enzymatic function after it inactivates the nucleic acid polymerization terminators by hydrolysis. This is because it does not degrade nucleotide triphosphate in a subsequent reverse transcription reaction or PCR reaction.

For example, the phosphatase may be BAP (bacterial alkaline phosphatase) or CIP (calf intestinal phosphatase), which has the property of degrading triphosphate. Preferably, CIP that is easily inactivated by heat is used.

In addition, an alkaline phosphatase (Autotaxin) (Clair T, Lee H Y, Liotta L A, Stracke M L (1997). "Autotaxin is an exoenzyme possessing 5'-nucleotide phosphodiesterase/ATP pyrophosphatase and ATPase activities". J. Biol. Chem. 272 (2): 996-1001. doi:10.1074/jbc.272.2.996. PMID 8995394.) may be used, which hydrolyzes pyrophosphate and ATP and is derived from various organisms, including *E. coli*, bovine small intestine, and shrimps. Also, *Staphylococcus aureus* adenosine synthase (AdsA) that non-specifically degrades nucleotide triphosphate may be used.

In the nucleic acid preparation method according to the present invention, subsequently to the nucleic acid separation/purification process, nucleic acid polymerase and a nucleic acid polymerization terminator may be added to the extracted nucleic acid to terminate the polymerization of the nucleic acid to thereby prevent the non-specific priming of the template nucleic acid. After the reaction, a step of removing unreacted nucleic acid polymerization terminators is required, because the unreacted nucleic acid polymerization terminators act as an inhibitor of a subsequent polymerase chain reaction or other PCR reactions.

Removal of the nucleic acid polymerization terminator may be performed using gel filtration, or a chaotropic agent and a silica bead, but is not limited thereto.

The nucleic acid preparation method according to the present invention may be performed using a known nucleic acid analyzer comprising a known automatic nucleic acid extraction system and a gene amplification system. Preferably, Exiprep 16 DX (Bioneer, Korea) as described above may be used, but is not limited thereto.

More specifically, subsequently to the nucleic acid separation/purification process, nucleic acid polymerase and a nucleic acid terminator may be added to the extracted nucleic acid to terminate the polymerization reaction of the nucleic acid and inactivate the priming function of all the nucleic acids. The terminator remaining after the termination acts as an inhibitor of a subsequent reverse transcription reaction or PCR reaction, and for this reason, two methods can be used to remove the remaining terminator: a method of performing RNA purification again using the Exiprep 16 DX system (Bioneer); and a method of degrading the nucleic acid polymerization terminator so as to no longer react.

The method of performing RNA purification using the Exiprep 16 DX system is a method in which RNA is attached to magnetic silica particles in the presence of a chaotropic agent and washed and eluted. This method has problems in that it is time-consuming because several steps are performed and in that the purified RNA is lost. On the other hand, the method of inactivating the activated nucleic acid polymerization terminator (nucleotide triphosphate) by degrading it into di- or mono-triphosphates has many advantages in that it is fast and simple and does not reduce the yield.

More specifically, in the method of inactivating the nucleic acid polymerization terminator using enzyme, the wells of Exiprep 16 DX, which contain magnetic particles and are used in the elution step, are temperature-controllable wells. Thus, after elution with elution buffer, the nucleic acid polymerization terminator can be easily can be removed by adding triphosphate hydrolase, such as alkaline phosphatase, autotoxin or *Staphylococcus aureus* adenosine synthase (AdsA) to the wells and reacting the enzyme at 37° C.

In another aspect, the present invention also relates to a method for preparing a composition for hot-start reverse transcription reaction or hot-start reverse transcription PCR.

Specifically, the preparation method comprises introducing a reaction mixture, which comprises a reaction buffer solution, $MgCl_2$, four kinds of dNTPs, reverse transcription polymerase, PPi and PPase, into a single reaction tube.

Particularly, in the preparation of the composition for hot-start reverse transcription PCR, the reaction mixture further comprises DNA polymerase.

The DNA polymerase may be one or more selected from the group consisting of a polymerase having 5'→3' exonuclease activity, a polymerase having 3'→5' exonuclease activity, and a polymerase that does not have 5'→3' exonuclease activity and 3'→5' exonuclease activity.

Preferably, the above preparation method further comprises a step of freezing or drying the reaction mixture to form a dry composition having increased stability and long-term storage stability, but is not limited thereto.

The pyrophosphate (PPi) is preferably contained at a concentration of 0.1-5 mM, and preferably 0.5-2.0 mM, and the pyrophosphatase is preferably contained in an amount of 0.005-0.25 U per 0.1 mM PPi, but is not limited thereto.

Additionally, the reaction mixture may comprise at least one selected from the group consisting of one or more primers or probes, a fluorescent dye that binds to DNA, template nucleic acid, a dye non-reactive with nucleic acid, a polyol, gelatin, bovine serum albumin, Thesit, and PEG-8000. Herein, the fluorescent dye may be selected from the group consisting of SyBr Green, EtBr and HRdye, and the dye may be one or more selected from the group consisting of rhodamine, tamra, lax, bromophenol blue, xylene cyanole, bromocresol red, and cresol red.

In still another aspect, the present invention is directed to a kit for hot-start reverse transcription reaction, which comprises the above-described composition for hot-start reverse transcription reaction.

The present invention is also directed to a kit for hot-start reverse transcription PCR, which comprises the above-described composition for hot-start reverse transcription PCR.

The kit may be prepared according to a conventional method for preparing a kit for reverse transcription reaction or a kit for reverse transcription PCR.

The present invention is also directed to a method of reverse transcription of template RNA, the method comprising the steps of: mixing the composition for hot-start reverse transcription reaction with a sample containing the template RNA to form a reaction mixture; and performing a reaction so that the reaction mixture can be reverse-transcribed.

The present invention also provides a method of amplifying nucleic acid, the method comprising the steps of: mixing the composition for hot-start reverse transcription PCR with a sample containing template RNA to obtain a reaction mixture; performing a reaction so as to amplify the reaction mixture to thereby obtain an amplification product; and analyzing the amplification product.

Herein, the reverse transcription PCR reaction may be any one or more of multiplex reverse transcription PCRs, real-time reverse transcription PCR, and real-time quantitative reverse transcription PCR.

In a preferred embodiment of the present invention, the template nucleic acid is preferably an RNA that may be amplified by reverse transcription and PCR.

The inventive composition for hot-start reverse transcription reaction and the inventive composition for reverse transcription PCR comprise, in addition to a reverse transcription reaction mixture comprising reaction buffer solution, $MgCl_2$, four kinds of dNTPs and reverse transcription polymerase, PPi and PPase, which can prevent a reverse transcription reaction from occurring in a mixing process at room temperature. In addition, PPi can be degraded to activate the reverse transcription polymerase by reacting PPase at a temperature equal to or higher than the temperature at which primers specifically hybridize, and thus a reverse transcription reaction can be initiated at the hybridization temperature so that non-specific cDNA synthesis can be eliminated. Thus, selectivity can be greatly increased compared to that of conventional reverse transcription reactions, and even a very small amount of the target RNA can be successfully detected. In addition, when the composition is frozen, or dried in a mixture with a stabilizer, it can be used in a stable and convenient manner compared to conventional compositions, and thus is useful as a more stable composition for hot-start reverse transcription reaction.

In an embodiment of the present invention, a hot-start reverse transcription was performed in the presence of PPi and PPase using a reverse primer exactly matching the template RNA and a primer having a nucleotide sequence mismatching the template RNA. As a result, the amplification product was detected in the reverse primer exactly matching the template RNA, but was not detected in the reverse primer having the nucleotide sequence mismatching the template RNA. On the contrary, it was found that, when a hot-start reverse transcription reaction was performed in the absence of PPi and PPase, the amplification product was detected even in the reverse primer having the mismatch nucleotide sequence.

In another embodiment of the present invention, the single-nucleotide polymorphism of the target RNA was analyzed using a hot-start reverse transcription PCR reaction. As a result, it was found that, when the hot-start reverse transcription reaction was performed in the presence of PPi and PPase, the results obtained using the primer exactly matching the template RNA did differ in PCR efficiency from the results obtained using the reverse primer having a single mismatch nucleotide. However, the hot-start reverse transcription reaction having no PPi and PPase was detected in the same cycle without difference between the matching reverse primer and the mismatch reverse primer. This suggests that the hot-start reverse transcription reaction according to the present invention makes it possible to analyze single-nucleotide polymorphism using a real-time PCR method, but in a reaction solution having no hot-start reverse transcription function, it is difficult to analyze single-nucleotide polymorphism.

In another embodiment of the present invention, the effect of the hot-start reverse transcription PCR reaction of the present invention on the inhibition of non-specific reactions resulting from the self-priming of single-stranded nucleic acids contained in extracted nucleic acids was examined. As a result, it was found that the hot-start reverse transcription reaction inhibited non-specific reactions resulting from self-priming, compared to a reaction solution having no hot-start function (that is, having no PPi and PPase).

In another embodiment of the present invention, the effect of RNA termination on the inhibition of non-specific reverse transcription PCR reactions resulting from RNA self-priming was examined. It was shown that, when an extracted RNA terminated with poly(A) polymerase and 3'-deoxyadenosine 5'-triphosphate (3'-dATP) at the 3' end was used as a template, cDNA was synthesized from non-terminated RNA even when any primer was not added. In other words, the cDNA was synthesized by self-priming and amplified in PCR. Also, the PCR amplification resulting from the non-specific cDNA synthesis could not be perfectly prevented even by the hot-start reverse transcription PCR reaction, and the reverse transcription PCR reaction by RNA self-priming could be partially inhibited, and thus the Ct value was reduced by about 5, indicating that the non-specific reaction could be inhibited by about 1/30.

However, it was shown that, in a sample comprising the RNA terminated at the 3' end, cDNA was not amplified up to 45 cycles in all the reverse transcription PCR reactions, indicating that no cDNA was synthesized. Such results suggest that many non-specific reverse transcription PCR reactions occur during mixed reverse transcription PCR reaction mixture, and for this reason, many non-specific cDNAs are made. Also, from the above results, it can be seen that undesired reactions cannot be inhibited by the hot-start reverse transcription PCR alone. As a result, it can be seen that such non-specific reverse transcription PCR reactions resulting from RNA self-priming can be perfectly inhibited by terminating the RNA using the termination reaction of the present invention.

In another embodiment of the present invention, it was found that, when the hot-start PCR of the present invention is used, the detection limit of a cancer marker is increased.

The nucleotide sequence information of *Homo sapiens* Keratin 8 (KRT8) as a cancer marker was obtained from the National Center for Biotechnology Information (NCBI, USA), and RNA was extracted from human Hela C cells and subjected to RNA termination. As a result, in the case of samples subjected to RNA termination, the cancer marker was detected in a hot-start reverse transcription reaction sample containing 10 or more Hela cells added to 1 ml of human serum. In the case of reactions having no hot-start reverse transcription reaction function, the caner marker was detected in the sample containing 100 or more Hela cells. In the case of samples comprising non-terminated RNA, the cancer marker was detected in hot-start reverse transcription reaction samples containing 100 or more Hela cells. In the case of reaction solutions having no hot-start reverse transcription function, the caner marker was detected in the samples containing 1,000 or more Hela cells.

Thus, it can be seen that the detection limit was increased even by the hot-start reverse transcription reaction alone, but a better effect could be obtained when the hot-start reverse transcription reaction was performed together with RNA termination.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

EXAMPLES

Hereinafter, the present invention will be described in further detail with reference to examples. It is to be understood, however, that these examples are for illustrative purposes only and are not intended to limit the scope of the present invention.

Example 1: Examination of the Effect of PPi on Inhibition of Reverse Transcription Reactions In order to examine the conditions in which a reverse transcription reaction is inhibited by PPi, a reverse transcription reaction was performed using 1.5 mM magnesium ion and varying concentrations of PPi, and the reaction product was subjected to PCR. Specifically, 0.5-2 mM of PPi was added to Accupower RT Premix (Bioneer, Korea), and a reverse transcription reaction and a PCR reaction were performed. The reverse transcription reaction was performed using 100 ng, 10 ng, 1 ng or 100 pg of RNA extracted from human Hela cells was added, in the presence of PPi added at a concentration of 0, 0.5, 1, 1.5, 2 or 2.5 mM. The reverse transcription reaction was performed once at 42° C. (the optimum temperature of Accupower RT Premix (Bioneer, Korea)) for 60 minutes, and was performed once at 95° C. for 5 minutes to inactivate reverse transcriptase. 5 µl of 20 µl of the reverse transcription reaction product was added to Accupower PCR Premix (Bioneer, Korea) and subjected to a PCR reaction using the GAPDH forward primer 5'-GGAAGGTGAAGGTCGGAGTC-3' (SEQ ID NO: 1) and the GAPDH reverse primer 5'-GCCAAAT-TCGTTGTCATACC-3' (SEQ ID NO: 2), which target the nucleotide sequences of human GAPDH primers. The PCR reaction was performed under the following conditions: pre-denaturation at 95° C. for 5 min, and then 30 cycles, with 95° C. for 20 sec, 55° C. for 40 sec, and 72° C. for 60 sec as one cycle, are followed by final extension at 72° C. for 5 min. The PCR reaction product was electrophoresed on agarose gel together with a DNA molecular weight marker, and then stained with ethidium bromide, and the DNA band amplified by the PCR reaction was photographed with a Polaroid camera. As a positive control, RT PreMix (Bioneer, Korea) containing no PPi was used, and the product was subjected to a PCR reaction.

Figure 1:
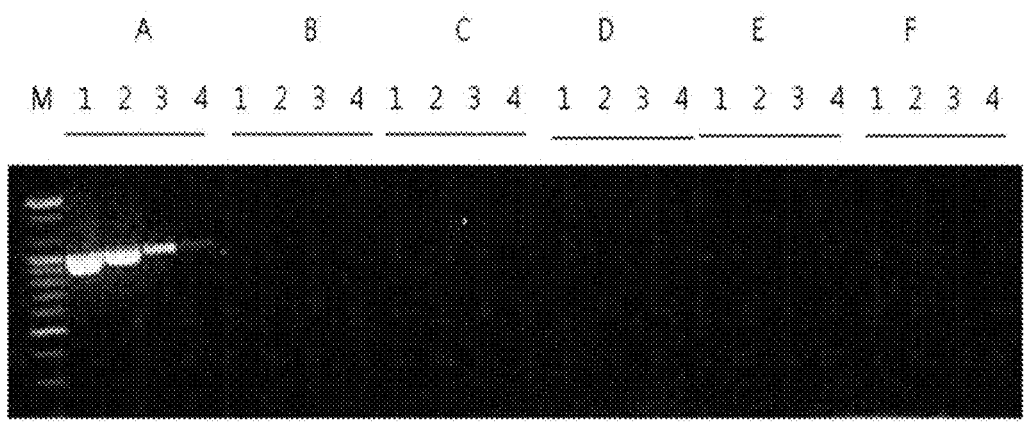
FIG. 1 shows the effect of pyrophosphate (PPi) on the inhibition of reverse transcription reactions:
Lanes 1, 2, 3 and 4: the results of performing reverse transcription reactions of 100 ng, 10 ng, 1 ng and 100 pg of RNA, respectively;
A: positive control results obtained by performing a reverse transcription reaction in the absence of PPi, followed by PCR reaction;
B, C, D, E and F: the results of performing reverse transcription reactions in the presence of varying concentrations of PPi, followed by PCR reactions; and
Lane M: 100-bp DNA ladder (Bioneer, Korea) for sizing of PCR products.

As a result, it could be seen that, in the experimental group containing PPi, the reverse transcription reaction was inhibited from a PPi concentration of 0.5 mM and was more clearly inhibited when 2 mM PPi was added (FIG. 1).

Example 2: Examination of Reverse Transcription by PPase that Hydrolyzes PPi into Two Phosphates The results of Example 1 indicated that reverse transcription reactions were inhibited by addition of PPi. For the reverse transcription reaction as described above, PPase that degrades PPi into two phosphates was added in order to examine the activation of the reverse transcription reaction. Specifically, under the condition in which PPi was added in the same manner as described in Example 1, 0.1 U of PPase was added, and a PPi enzyme reaction and a reverse transcription reaction were simultaneously performed at 42° C. for 60 minutes. Then, the reaction product was allowed to stand at 95° C. for 5 minutes in order to inactivate the reverse transcriptase, and was then subjected to PCR.

Figure 2:
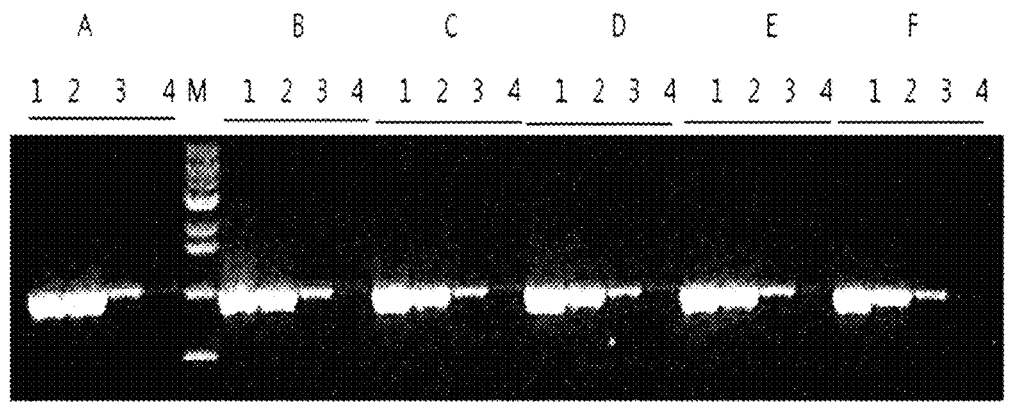
FIG. 2 shows that reverse transcription reactions are activated again by adding pyrophosphatase (PPase) that hydrolyzes PPi into two phosphates:
Lanes 1, 2, 3 and 4: the results of performing reverse transcription reactions of 100 ng, 10 ng, 1 ng and 100 pg of RNA, respectively;
A: positive control results obtained by performing a reverse transcription reaction in the absence of PPi, followed by PCR reaction;
B, C, D, E and F: the results obtained by adding varying concentrations of PPi;
B-1, C-1, D-1, E-1 and F-1: the results of performing reverse transcription reactions in the presence of PPase, followed by PCR reactions;
Lane M: 1-kb DNA ladder.

As a result, it was found that, when PPase was added, PCR was activated to maximize the amount of the PCR product (FIG. 2).

Example 3: Examination of Real-Time Reverse Transcription PCR in the Presence of PPi and PPase In order to examine a real-time reverse transcription PCR reaction by a composition containing PPi and PPase, 2 mM PPi and 0.1 U PPase were added 2×PCR PreMix solution (containing 10 mM Tris HCl pH 9.0, 50 mM KCl, 1.5 mM $MgCl_2$, four kinds of dNTPs (each 250 uM), 1 U tag DNA polymerase, 200 U reverse transcriptase, 1 mM DTT, 0.01% Tween 20, and stabilizer), and a reaction was performed using 25 µl of the PCR PreMix solution. The forward primer 5'-CGTGGAAGGACTCATGACCACA-3' (SEQ ID NO: 3), the reverse primer GCCTTGGCAGCGCCAGTAGA-3' (SEQ ID NO: 4) and the GAPDH probe 5'-CTGTGGATG-GCCCCTCCGGGAAA-3' (SEQ ID NO: 5), which target the human GAPDH gene, were synthesized and each was added at a concentration of 10 nM. As template RNA, total RNA extracted from Hela cells was used in an amount of 100 ng, 10 ng, 1 ng or 100 pg. Then, distilled water was added to the mixture to a final volume of 50 µl. Real-time reverse transcription PCR was performed using Exicycler 96 Real-Time Quantitative Thermal Block (Bioneer, Korea) under the following conditions: reverse transcription at 50° C. for 15 minutes, and then pre-denaturation at 95° C. for 5 min, and then 45 cycles, each cycle consisting of denaturation at 95° C. for 5 sec, annealing at 60° C. for 5 sec, extension at 72° C. for 6 sec, and scanning for detection of fluorescence.

Figure 3:
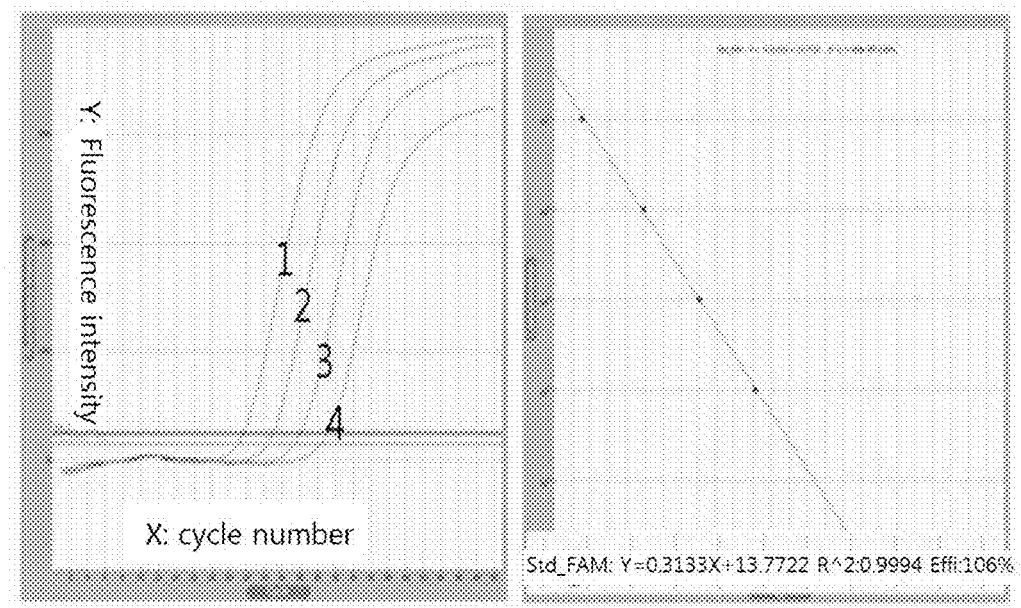
FIG. 3 shows the effects of addition of PPi and PPase on real-time reverse transcription PCR:
Lanes 1, 2, 3 and 4: the results of real-time reverse transcription PCR using 100 ng, 10 ng, 1 ng and 100 pg of human total RNA.

As a result, it was shown that PPi and PPase did not influence the real-time reverse transcription PCR, and a standard graph having a slope of −3.1 and a linear $R^2$ value of 0.9994 was plotted (FIG. 3).

Example 4: Detection of Hepatitis C Virus RNA by Hot-Start Reverse Transcription Reaction To perform real-time reverse transcription PCR, template RNA was prepared. Specifically, a Hepatitis C virus gene was synthesized by a gene synthesis method (see Biochem. Biophys, Res. Commun 1998, 248, 200-203), and a portion thereof was cloned into a pGEM-T-Easy vector (Cat. A1360, Promega, USA). Specifically, 5 µl of 2× rapid ligation buffer (Promega, USA), 1 µl of T-easy vector (Promega, USA), 1 µl of T4 DNA ligase (Promega, USA), and 3 µl (8 ng) of the synthesized gene were placed and mixed in the same tube, and then incubated to stand at 37° C. for 1 hour. Next, 5 µl of the incubated reaction solution was added to 50 µl of *E. coli* competent cells, kept on ice for 40 minutes, incubated at 42° C. for 40 seconds, and then kept on ice for 2 minutes. The reaction solution was seeded into an LB plate containing ampicillin, isopropyl 1-thio-β-D-galactoside (IPTG) and X-gal, and was then incubated at 37° C. for 16 hours. After incubation, white colonies were taken, incubated in LB liquid medium for 16 hours and then centrifuged. The supernatant was removed, and plasmid DNA was extracted from the pellet using an AccuPrep Plasmid Prep kit (Bioneer, Korea). When the plasmid DNA had a purity of 1.8-2.0 as measured by an UV spectrophotometer (Shimazu, Japan), the plasmid DNA was transcribed into RNA using a MAXIscript In vitro transcription kit (Ambion, USA. After transcription, when the RNA had a purity of 1.8-2.0 as measured by an UV spectrophotometer, it was used as template RNA in a subsequent real-time reverse transcription PCR. The copy number of the RNA was calculated using the following equation 1:

$$6.02\times10^{23}\times\text{concentration (g/ml, measured by UV spectrophotometer)}/(3015+150)\times340 \quad \text{Equation 1}$$

wherein 3015 represents the size of T-vector (3015 bp), and 150 represents the size of hepatitis C virus template RNA (150 bp). After calculating the copy number of the template RNA was serially 10-fold diluted with 1×TE buffer (10 mM Tris-HCl, pH 8.0, 0.1 mM EDTA) and was stored at −70° C. until use. Using the constructed RNA as a template, real-time reverse transcription PCR was performed using 30 nM of the hepatitis C virus forward primer 5'-ACCGGGTC-CTTTCTTGGAT-3' (SEQ ID NO: 6), the reverse primer 5'-CCCTATCAGGCAGTACCACA-3' (SEQ ID NO: 7) and the probe [5'FAM]-CGTGCCCCGCRAGACTGCT-[3'BHQ1] (SEQ ID NO: 8). The reactants used in the real-time reverse transcription PCR were the same as described in Example 3, and the template RNA with a copy number of $10^{10}$, $10^9$, $10^8$, $10^7$, $10^6$, $10^5$, $10^4$, $10^3$, $10^2$ or 10 was added. The reaction was performed in the same manner as described in Example 3, except for the primer, the probe and the template RNA.

Figure 4:
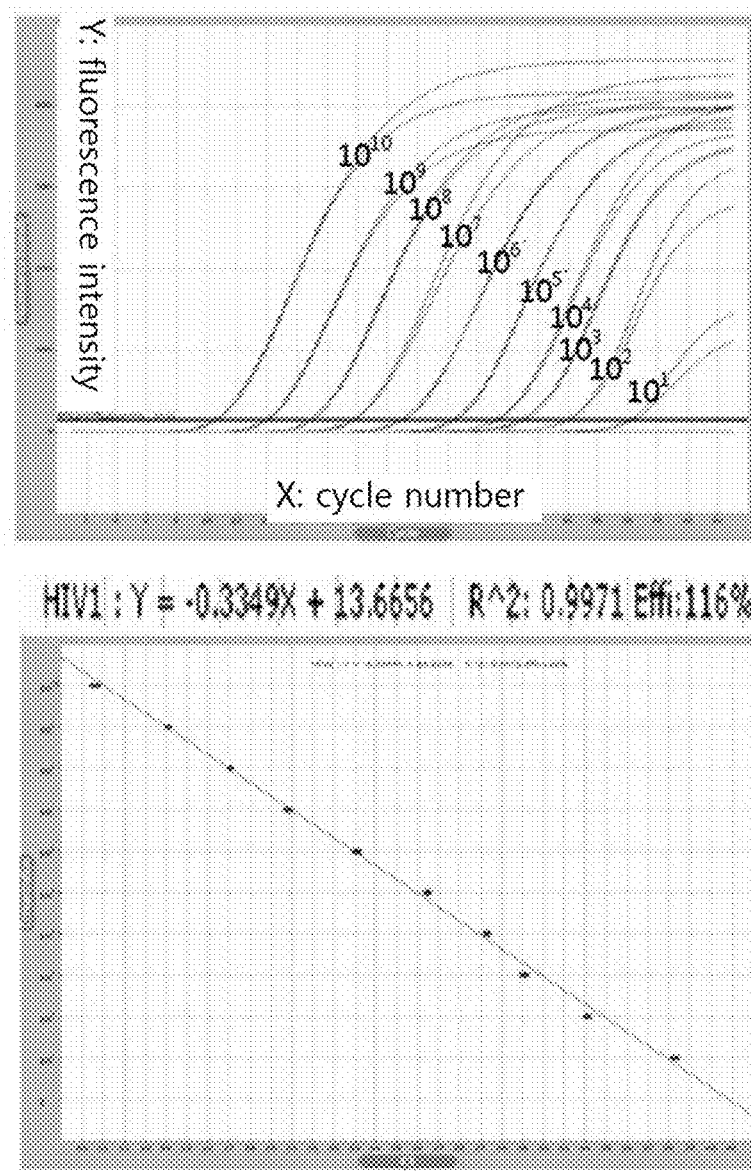
FIG. 4 shows the results of detecting hepatitis C virus RNA by a hot-start reverse transcription reaction.

As a result, the template RNA with a copy number ranging from $10^{10}$ to 10 could be detected and a standard graph of the standard template real-time reverse transcription PCR that was repeated twice showed a slope of −3.21 to −3.73 and a linear $R^2$ value of 0.995-0.998 (FIG. 4). Herein, $R^2$ is a correlation ship that indicates the linearity of the plotted standard graph of the real-time PCR, and a $R^2$ closer to 1 (closer to a straight line) indicates that PCR was more accurately performed.

Example 5: Examination of the Effect of PPi and PPase on Inhibition of Non-Specific Reaction in Real-Time Reverse Transcription PCR In order to examine the effect of PPi and PPase on the non-specific reaction of purified RNA in an actual clinical sample, 1 μg of total RNA extracted from Hela cells in addition to the target template RNA was added to the same primers, probe and real-time reverse transcription PCR solution as described in Example 4. As a control, a reaction solution having no hot-start reverse transcription function (that is, having no PPi and PPase) was used. In order to examine the inhibition of non-specific reactions, 1 μg of total RNA extracted from human cells was added to and reacted with each of a hot-start reverse transcription reaction solution and a reaction solution having no hot-start reverse transcription function. This Example was performed in the same manner as described in Example 4, except that the extracted RNA was added.

Figure 5A:
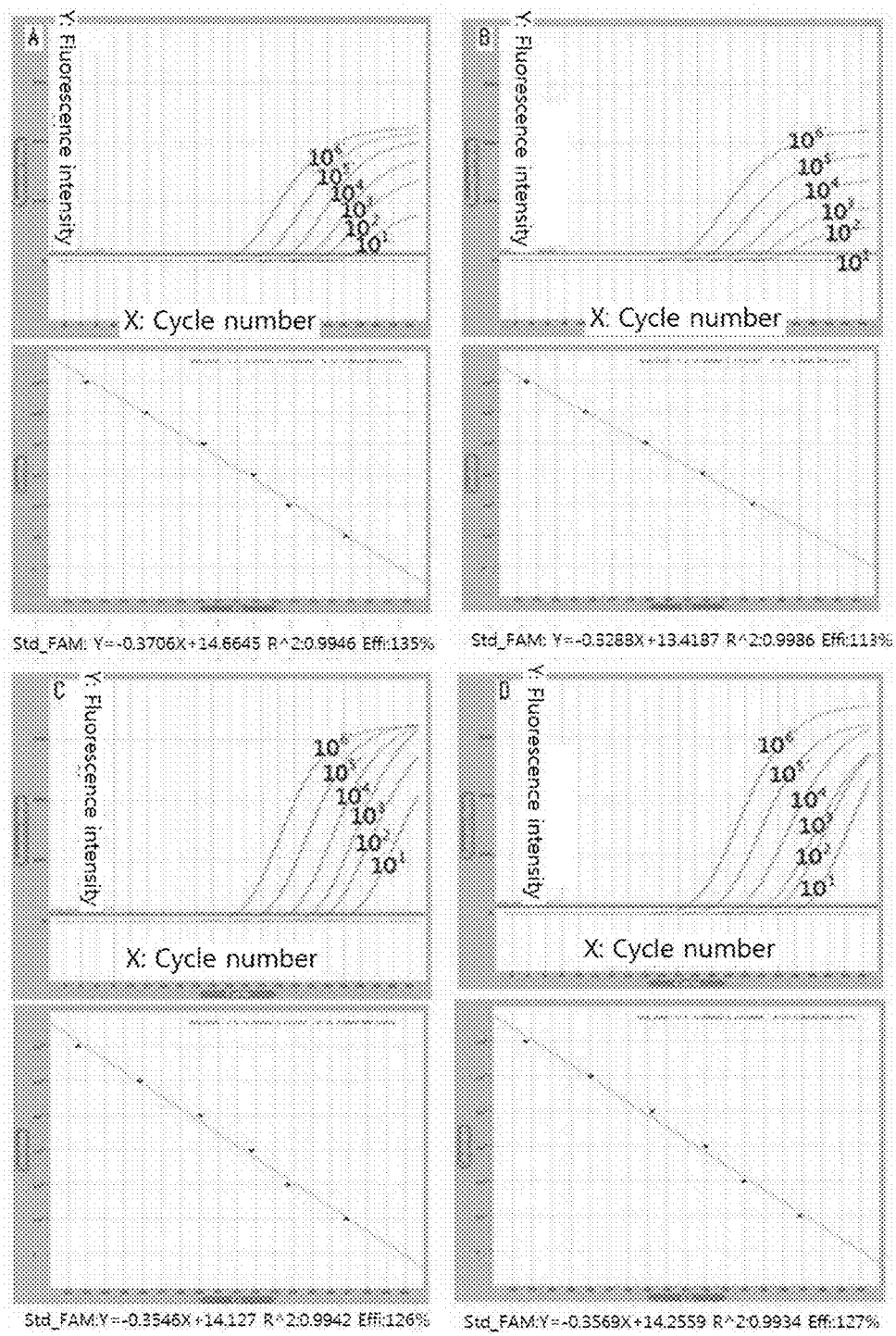
FIG. 5a shows the effects of PPi and PPase on the inhibition of non-specific reactions in real-time reverse transcription PCR:
A: the results obtained using a reaction solution having no hot-start reverse transcription function;
B: the results obtained from adding 1 μg of total RNA of human cell to the reaction solution of "A";
C: the results obtained using a hot-start reverse transcription reaction solution comprising PPi and PPase; and
D: the results obtained from adding 1 μg of total RNA of human cell to the reaction solution of "C".
Figure 5B:
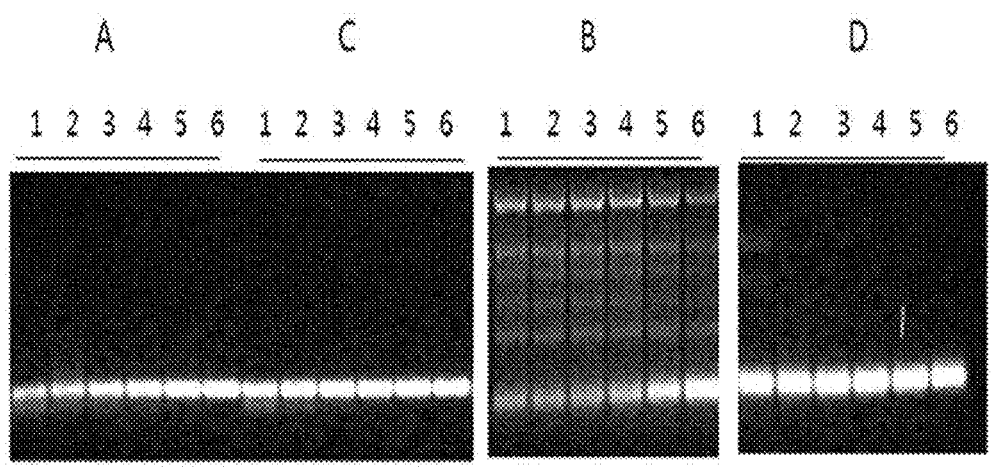
FIG. 5b shows the results of electrophoresis of real-time reverse transcription PCR products on 2% agarose gel.

As a result, it was found that, when the hot-start reverse transcription reaction was performed in the presence of PPi and PPase, non-specific reactions by RNAs other than the target RNA were inhibited, and RNAs other than the target RNA did not result in a decrease in reaction efficiency and changes in sensitivity and detection ability. However, it was shown that, in the hot-start reverse transcription that was performed in the absence of PPi and PPase, non-specific reactions were caused by the added human cell RNA, and reaction efficiency, detection ability and sensitivity significantly decreased (FIG. 5a). The product from the real-time reverse transcription PCR was analyzed by electrophoresis on 2% agarose gel, and as a result, it was found that, in case of the product not subjected to the hot-start reverse transcription reaction, non-specific reactions more actively occurred due to the total RNA extracted from the human cells (FIG. 5b). Thus, it can be seen that problems such as a decrease in reaction efficiency in non-specific reactions in reverse transcription PCR reactions can be solved by a hot-start reverse transcription reaction in the presence of PPi and PPase.

Example 6: Comparison of Inhibition of Non-Specific Reactions Between Use of Hot-Start Reverse Transcription Reaction and Use of Hot-Start PCR in Real-Time Reverse Transcription PCR In order to examine which of a hot-start reverse transcription reaction and a hot-start PCR is more effective in reaction specificity and sensitivity in real-time reverse transcription PCR, the following experiment was performed. In addition to the same primers, probe and real-time reverse transcription PCR reaction solution as described in Example 5, target template RNA and 1 μg of total RNA extracted from human cells were used. A reaction solution having no hot-start reverse transcription function (that is, having no PPi and PPase) was used in a hot-start PCR reaction mix comprising Taq antibody. To examine the effect of the hot-start reverse transcription reaction on the inhibition of non-specific reactions, PPi and PPase were added to a hot-start PCR reaction mix comprising Taq antibody, and a hot-start reverse transcription reaction and a hot-start PCR were simultaneously used.

As a result, it was found that, in reverse transcription and PCR, non-specific reactions could not be inhibited by the hot-start PCR reaction alone, and when the hot-start reverse transcription reaction was performed in the presence of PPi and PPase, non-specific reactions for a large amount of RNA could be inhibited. Also, it was shown that the hot-start PCR reaction employing Taq antibody inhibited non-specific PCR reactions at low temperature, but could not inhibit non-specific reactions in the reverse transcription reaction. Thus, it can be seen that the hot-start reverse transcription reaction is required to eliminate non-specific reactions in the reverse transcription reaction and the PCR reaction. In both the reverse transcription reaction and the PCR reaction, non-specific reaction products decreased in the PCR reaction performed using Taq antibody (B of FIG. 6b) compared to those in the reaction having no hot start function (B of FIG. 5b), non-specific reactions still occurred, and thus it was difficult to detect disease virus such as the target hepatitis C virus DNA having a copy number of 100 or less in samples containing large amounts of human RNAs derived from human cells (B of FIG. 6a). On the other hand, in the reaction comprising PPi and PPase, non-specific reactions by RNA derived from human cells did not occur (D of FIG. 6b), the target hepatitis C virus DNA with a copy number of 10 or more could be detected with high density (D of FIG. 6a).

Example 7: Examination of Standard Template Real-Time Reverse Transcription PCR Using a Dry-Type Reverse Transcription/PCR Composition In order to examine the thermal stability of a dry material of reverse transcription/PCR mixture solution, a PCR mixture solution containing PPi and PPase as described in Example 4 was prepared and dried, and real-time reverse transcription PCR was performed in an Exicycler Quantitative Thermal Block (Bioneer, Korea) using the dried mixture. Specifically, 5 μl of 10× buffer, 3 U of Taq DNA polymerase, 5 μl of dNTP 20 mM, PPi, PPase, stabilizer and the like were introduced into a single tube, and distilled water was added to a total volume of 25 μl. The mixture solution was dispensed into the tube of Exicycler Quantitative Thermal Block (Bioneer, Korea) and dried using SuperCentra (Bioneer, Korea) for 50-60 minutes. Next, the primers and probe used in Example 4 were mixed with each other to a total volume of 5 μl and added to the dried mixture, followed by drying for 30 minutes. To the dried mixture, the template RNA as used in Example 6 was added, and distilled water was added thereto to a total volume 50 μl, and the resulting solution was sufficiently mixed so that the dried material was easily dissolved. Real-time reverse transcription PCR was performed in the same manner as described in Example 4, except that Exicycler Quantitative Thermal Block (Bioneer, Korea) was used, a negative control (blank sample having no template RNA) was also reacted, and a template RNA with a copy number of $10^6$, $10^5$, $10^4$, $10^3$, $10^2$ or 10 was used.

As a result, like Example 4, the template RNA with a copy number of 10 or more could be detected, and when the standard graph of the standard template real-time reverse transcription PCR was plotted, it showed a slope of −0.2932 and an $R^2$ value of 0.9991. The above results suggest that the dried mixture showed the same performance as a solution-state mixture in real-time reverse transcription PCR (FIG. 7).

Example 8: Test for Stability of Dried Reverse Transcription/PCR Reaction Composition at Various Storage Periods Using the same composition and method as described in Example 7, a PCR mixture containing PPi and PPase was prepared, and then stored at 50° C. at 1-day intervals for 8 days. Then, the dried PCR composition according to each storage period was treated using Exicycler96 Quantitative Thermal Block, and the template RNA was used with a copy number of $10^6$, $10^5$, $10^4$ or $10^3$, and real-time reverse transcription PCR was performed under the same conditions as described in Example 7. This is a method making it possible to predict the period of maintenance of performance of the dried composition at −20° C. (actual recommended storage temperature) by an accelerated test. When the composition was stored at 40° C. for 1 day, it is regarded to be stored at −20° C. for about 128 days. Specifically, the dried composition was prepared in an amount corresponding to 6 tests, and was dried. Immediately after drying, a portion of the dried mixture was prepared in an amount corresponding to 5 tests under the same conditions as described in Example 7. Then, real-time reverse transcription PCR was performed in the same manner as described in Example 4, except that the template RNA was used with a copy number of $10^6$, $10^5$, $10^4$ or $10^3$, thereby obtaining the results of a control. The dried composition was stored in an incubator at 50° C., and the amount required for the reaction was taken at one-day intervals and subjected to real-time reverse transcription PCR. At this time, the reaction was performed using four copy numbers (ranging from $10^3$ to $10^6$) of RNA. The dried composition stored for each period was subjected to real-time reverse transcription PCR reaction using Exicycler96 Quantitative Thermal Block (Bioneer, Korea), and among the results of the reaction with dried mixtures classified by storage days, the slope value and the $R^2$ value were compared with those of the control group, thereby comparing the performance of the dried mixture immediately after preparation with that of the dried mixture stored at 50° C. for each period.

As a result, the liquid mixture (control group) stored at 50° C. at 1-day intervals for 5 days showed a slope of −0.345 and an $R^2$ value of 0.9922, and the dried composition stored at 50° C. showed a slope of −0.31 to −0.34 and an $R^2$ value of 0.995-0.998. In other words, the results after 5 days of storage at 50° C. were equal to the results immediately after drying, and such results were substantially similar to the results obtained after storage for about 640 days at −20° C. (FIGS. 8a and 8b).

Example 9: Inhibition of Non-Specific Binding of Primers by Hot-Start Reverse Transcription PCR Reaction To induce the non-specific binding of primers, the nucleotide sequence of the reverse primer among the primers and probe used in Example 4 was synthesized as shown in Table 2 below.

(SEQ ID NO: 7)
Reverser primer 5'-CCCTATCAGGCAGTACCACA-3'

TABLE 2

| | Nucleotide sequence |
|---|---|
| Reverse primer | 5'-CCCTATCAGGCAGTACCACA-3' (SEQ ID NO: 7) |
| Reverse primer having 6 mismatch nucleotides at the 5' end | 5'-GGGGGGCAGGCAGTACCACA-3' (SEQ ID NO: 9) |
| Primer having 6 mismatch nucleotides in the middle of the nucleotide sequence | 5'-CCCTATTTTTTTGTACCACA-3' (SEQ ID NO: 10) |

In order to examine the effect of non-specific primers, each of a reverse primer exactly matching the target template RNA, a reverse primer (SEQ ID NO: 9) having 6 mismatch nucleotides at the 5' end, and a primer (SEQ ID NO: 10) having 6 mismatch nucleotides in the middle of the nucleotide sequence was used. As a control, a reaction solution having no hot-start reverse transcription function (that is, having no PPi and PPase) was used. In order to examine whether non-specific primers cause false positive results, whether each reverse primer cause non-specific reactions was examined using a hot-start reverse transcription reaction solution and a reaction solution having no hot-start reverse transcription function. The procedure of Example 4 was repeated, except that the mismatch reverse primer was used and only a template RNA with a copy number of $10^4$ was used.

FIG. 9a shows the results of performing a real-time reverse transcription PCR using the primer having 6 mismatch nucleotides at the 5' end, and FIG. 9b shows performing a real-time reverse transcription PCR using the primer having 6 mismatch nucleotides in the nucleotide sequence. In FIG. 9, "A" indicates the results of performing the reaction using the reaction solution having no host-start reverse transcription function, and "B" indicates the results of performing the reaction using the hot-start reverse transcription PCR reaction mixture.

As a result, in the case of the hot-start reverse transcription performed in the presence of PPi and PPase, the amplification product was detected in the reverse primer exactly matching the template RNA, but was not detected in the reverse primer having mismatch nucleotides. However, in the case of the hot-start reverse transcription performed in the absence of PPi and PPase, the amplification product was detected even in the reverse primer having mismatch nucleotides. This suggests that enzymatic reactions occur due to the non-specific reaction of the reverse primer at a temperature lower than the reaction temperature (FIGS. 9a and 9b). Thus, it can be seen that problems such as false positive results caused by non-specific reactions in the reverse transcription PCR reaction can be solved by the hot-start reverse transcription reaction in the presence of PPi and PPase.

Example 10: Analysis of Single-Nucleotide Polymorphism by Hot-Start Reverse Transcription PCR Reaction To analyze the single-nucleotide polymorphism of the target RNA using the hot-start reverse transcription PCR reaction of the present invention, a reverse primer was designed such that it contains a point mutation. The nucleotide sequence of the reverse primer among the primers and probe used in Example 4 was synthesized as shown in Table 3 below.

TABLE 3

| | Nucleotide sequences |
|---|---|
| Reverse primer | 5'-CCCTATCAGGCAGTACCACA-3' (SEQ ID NO: 7) |
| Reverse primer having a single mismatch nucleotide | 5'-CCCTATCAGGCAGTCCCACA-3' (SEQ ID NO: 11) |

For analysis of single-nucleotide polymorphism, a reverse primer exactly matching the template RNA and a reverse primer having a single mismatch nucleotide were used. As a control, a reaction solution having no hot-start reverse transcription function (that is, having no PPi and PPase) was used. In order to examine whether the analysis of single-nucleotide polymorphism is possible, a reaction for each reverse primer was analyzed using a hot-start reverse transcription reaction solution and a reaction solution having no hot-start reverse transcription function. The analysis was performed in the same manner as described in Example 4, except that a reverse primer having a mismatch nucleotide was used and a template RNA with a copy number of $10^4$ was used. FIG. 10a shows the results of the hot-start reverse transcription PCR reaction, and FIG. 10b shows the results of performing the reaction using the reaction solution having no hot-start reverse transcription function. In FIG. 10, "A" indicates the results obtained using the primer having an exactly matching nucleotide sequence, and "B" shows the results obtained using the primer having a single mismatching nucleotide.

As a result, it was found that, when the hot-start reverse transcription reaction was performed in the presence of PPi and PPase, the results obtained using the primer exactly matching the template RNA did differ in PCR efficiency from the results obtained using the reverse primer having a single mismatch nucleotide. However, the hot-start reverse transcription reaction performed in the absence of PPi and PPase was detected in the same cycle without difference between the exactly matching reverse primer and the mismatch reverse primer. This suggests that the hot-start reverse transcription reaction makes it possible to analyze single-nucleotide polymorphism using a real-time PCR method, but in a reaction performed in the absence of a hot-start reverse transcription reaction mixture, it is difficult to analyze single-nucleotide polymorphism (FIGS. 10a and 10b). Thus, it was found that the hot-start reverse transcription reaction enables single-nucleotide analysis for the template RNA and can be used in various fields.

Example 11: Inhibition of RNA-RNA Self-Priming by Hot-Start Reverse Transcription Reaction The effect of the hot-start reverse transcription PCR reaction of the present invention on the inhibition of non-specific reactions resulting from self-priming of a single-stranded nucleic acid contained in an extracted nucleic acid was examined.

Total RNA was extracted from $10^6$ Hela cells using AccuZole Total RNA Extraction solution (Bioneer, Korea), and a final volume of 50 μl was obtained using DEPC-D.W.

The extracted RNA was quantified using NanoDrop 2000 (Thermo Scientific, USA), and 2 μg of the RNA was used. A reverse transcription reaction was performed using a reaction solution having no hot-start reverse transcription function (that is, having no PPi and PPase) as a control. A real-time PCR reaction was performed using AccuPower Dualstar qPCR Premix kit (Bioneer, Korea). The real-time PCR reaction was performed using the forward and reverse primers and probe used in Example 3. The reverse transcription reaction was performed using the primer 5'-TTTTTTTTTTTTTTTTTT-3' (SEQ ID NO: 12).

In order to examine whether the extracted RNA contains genomic DNA, a reverse transcription reaction was performed using a reaction solution having no hot-start reverse transcription function (that is, having no PPi and PPase) as a control, and the extracted total RNA as a template was subjected to real-time PCR using AccuPower Dualstar qPCR Premix (Bioneer, Korea) without reverse transcription reaction.

In FIG. 11, A shows the results of performing a real-time PCR reaction using RNA alone without reverse transcription reaction; and B shows the results of performing a reverse transcription reaction using the primer and then performing a real-time PCR reaction. B-A in FIG. 11 indicates the result of performing a hot-start reverse transcription reaction, and B-B indicates the result of performing a reaction using a reaction solution having no hot-start reverse transcription function.

FIG. 11C shows the results of performing a reverse transcription reaction using RNA alone in a reaction solution having no hot-start reverse transcription function and then performing a real-time PCR reaction. FIG. 11D shows the results of performing a reverse transcription reaction using RNA alone in a hot-start reverse transcription reaction mixture and then performing a real-time PCR reaction.

As a result, it was found that no detection was found in the absence of reverse transcription reaction, suggesting that the extracted total RNA contained no genomic DNA.

As a control, a reaction solution having no hot-start function (that is, having no PPi and PPase), and a reverse transcription reaction was performed using total RNA alone in the reaction solution without adding a primer. The reverse transcription reaction was performed at 50° C. for 1 hour and 95° C. for 5 minutes. A real-time PCR reaction was performed 5 μl of the reverse transcription reaction product as a template.

As a result, in the reaction solution having no hot-start function (that is, having no PPi and PPase), detection was found at 37 C(t) by self-priming, and in the hot-start reverse transcription reaction solution, detection was found at 41 C(t) (FIG. 11). Thus, it was found that non-specific reactions by self-priming were more inhibited in the hot-start reverse transcription reaction solution compared to those in the reaction solution having no hot-start function (that is, having no (PPi and PPase).

Example 12: Effect of RNA Termination on Inhibition of Non-Specific Reverse Transcription PCR Caused by RNA Self-Priming (1) Termination Reaction of RNA Fragment with Poly(A) Polymerase and 3'-Deoxyadenosine 5'-Triphosphate (3'-dATP)

Using an RNA extraction kit as described in Example 11, RNA was extracted from human HeLa C cells. The 3' end of the extracted RNA was terminated with poly(A) polymerase and 3'-deoxyadenosine 5'-triphosphate (3'-dATP) (C and D).

To remove the remaining 3'-deoxyadenosine 5'-triphosphate (3'-dATP), the terminated RNA was purified using AccuPrep PCR Purification kit (Bioneer, Korea). For comparison, RNA (A and B) which was not terminated at the 3' end were purified in the same manner as above. To examine the effect of a hot-start reverse transcription PCR, a PCR reaction was performed in each of the hot-start reverse transcription PCR reaction solution (B and D) and the PCR reaction solution having no hot-start function (A and C).

5 µg of RNA was used in each PCR reaction. A general PCR reaction was performed using AccuPower RocketScript RT Premix (Bioneer, Korea), and the hot-start PCR reaction was performed using AccuPower RocketScript RT Premix (Bioneer, Korea), which comprises pyrophosphate and phosphatase added thereto and distilled water added thereto to a final volume of 20 µl. To examine of RNA self-priming, any primer required for reverse transcription PCR was not added.

The reverse transcription PCR was performed using Mygenie Gradient Thermal Block (Bioneer, Korea), and to examine the effect of RNA self-priming during mixing of reactants, the PCR reaction mixture was incubated at 25° C. for 20 minutes.

To examine whether the reverse transcription PCR is caused by RNA self-priming, real-time reverse transcription PCR was performed using each reverse transcription PCR reaction mixture as a template, AccuPower Dualstar qPCR Premix (Bioneer, Korea) and the human GAPDH-targeting primers and probe used in Example 3.

The real-time PCR was performed using Exicycler 96 Real-Time Quantitative Thermal Block (Bioneer, Korea) under the following conditions: pre-denaturation at 95° C. for 5 min, and then 45 cycles, each cycle consisting of denaturation at 95° C. for 5 sec, annealing and extension at 60° C. for 5 sec, and scanning for fluorescence detection.

The results are shown in FIG. 12. As can be seen therein, in the case of the non-terminated RNAs (A and B), the human GAPDH gene was detected, suggesting that cDNA was synthesized even when no primer was added. This result indicates that cDNA was synthesized by self-priming and amplified in PCR.

Also, the PCR amplification resulting from the non-specific cDNA synthesis could not be perfectly prevented by the hot-start reverse transcription PCR reaction alone, and the reverse transcription PCR reaction caused by RNA self-priming could be partially inhibited, and thus the Ct value was reduced by about 5, indicating that the non-specific reaction could be inhibited by about 1/30.

However, it was shown that, in the samples comprising the RNA terminated at the 3' end (C and D), cDNA was not amplified up to 45 cycles in all the reverse transcription PCR reactions, indicating that no cDNA was synthesized. Above results suggest that many non-specific reverse transcription PCR reactions occur during mixed reverse transcription PCR reaction mixture, and for this reason, many non-specific cDNAs are made. From the above results, it can be seen that undesired reactions cannot be inhibited by the hot-start reverse transcription PCR reaction alone. As a result, it can be seen that such non-specific reverse transcription PCR reactions resulting from RNA self-priming can be perfectly inhibited by terminating RNA using the termination reaction of the present invention.

In FIG. 12, "A" and "B" show the results obtained using non-terminated RNA, and C and D show the results obtained using the terminated RNA. Also, for "A" and "C", a general reverse transcription reaction was performed, and for "B" and "D", the hot-start reverse transcription reaction was performed.

Example 13: Increase in Detection Limit of Cancer Marker by RNA Termination and Hot-Start Reverse Transcription PCR The nucleotide sequence information of *Homo sapiens* Keratin 8 (KRT8; Accession No. NM_00125693) as a cancer marker was obtained from the National Center for Biotechnology Information (NCBI, USA). Using the RNA extraction kit as described in Example 11, RNA was extracted from human Hela C cells. Real-time reverse transcription PCR was performed using 850 ng, 85 ng, 8.5 ng, 0.85 ng or 0.085 ng of the extracted RNA as a template, 30 nM of the forward primer 5'-GGAGCAGATCAAGACCCTCA-3' (SEQ ID NO: 13), the reverse primer 5'-TTGTCCATGTT-GCTTCGAGC-3' (SEQ ID NO: 14) and the probe [5'FAM]-TGCTGCTCCAGGAACCGTACCTTGT-[3'BHQ1] (SEQ ID NO: 15) in order to obtain a standard curve for performing quantitative analysis using a hot-start reverse transcription PCR reaction.

The results are shown in FIG. 13*a*.

In order to examine detection limit, 10,000, 1,000, 100 or 10 Hela cells were added to 1 ml of human serum, and RNA extraction and quantification were performed as described in Example 11.

As a result, it was found that the RNA concentrations were 57.5 ng/µl, 53.8 ng/µl, 52.5 ng/µl and 52.1 ng/µl. 500 ng of each extracted RNA was terminated according to the method of Example 12, and then quantified. To examine the effect of RNA termination on the detection limit, non-terminated RNA was used as a control. Real-time reverse transcription PCR was performed using 100 ng of each RNA in each of a reaction solution having no hot-start reverse transcription function (that is, having no PPi and PPase) and a hot-start reverse transcription PCR reaction solution. The real-time reverse transcription PCR was performed using Exicycler 96 Real-Time Quantitative Thermal Block (Bioneer, Korea) under the following conditions: reverse transcription reaction at 50° C. for 15 minutes, and then pre-denaturation at 95° C. for 5 min, followed by total 45 cycles, each cycle consisting of denaturation at 95° C. for 5 sec, annealing at 60° C. for 5 sec, extension at 72° C. for 6 sec, and scanning for fluorescence detection.

Figure 13B:
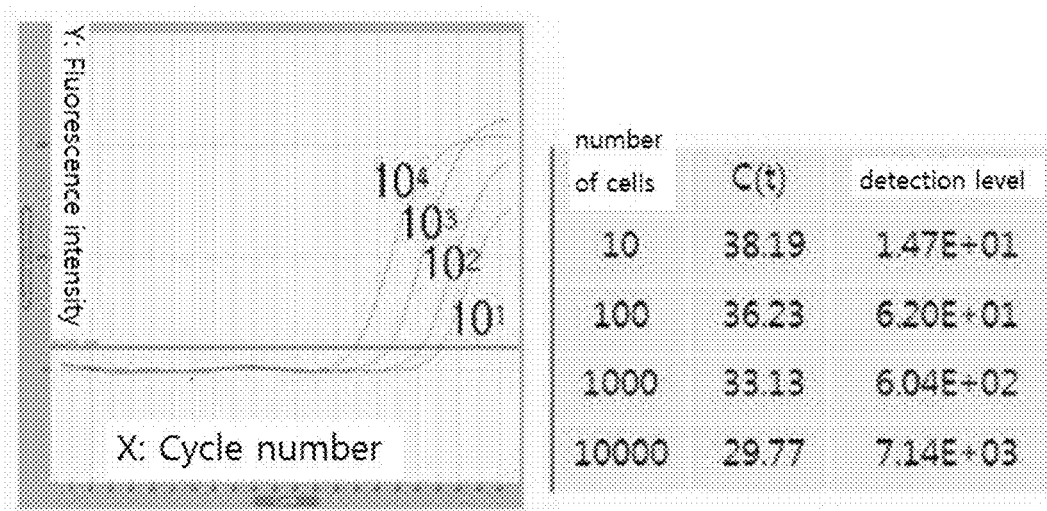
Figure 13C:
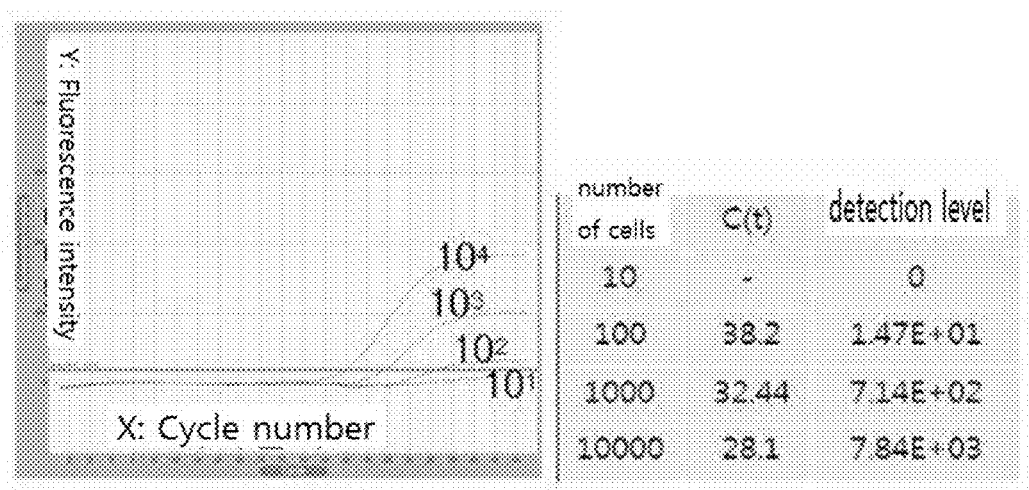
Figure 13D:
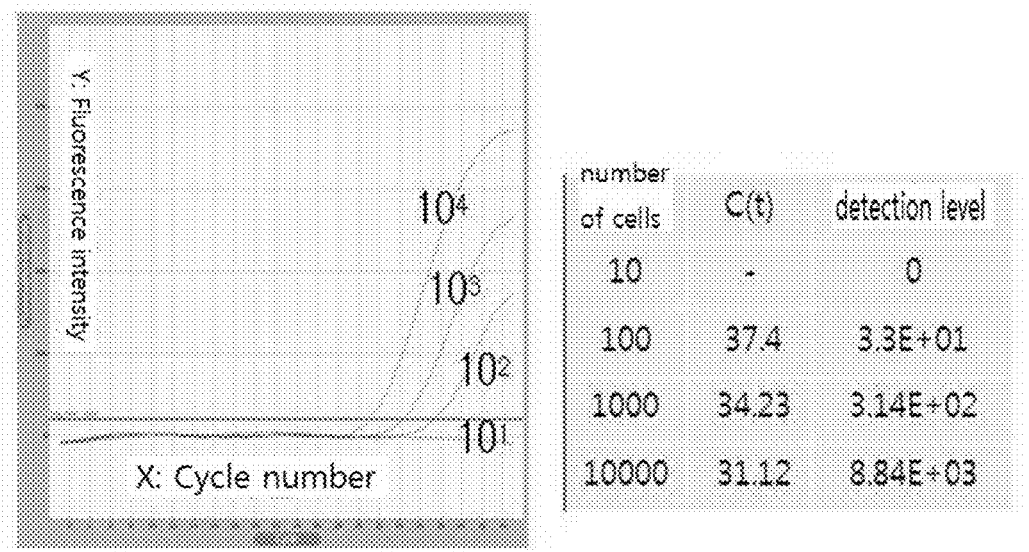
Figure 13E:
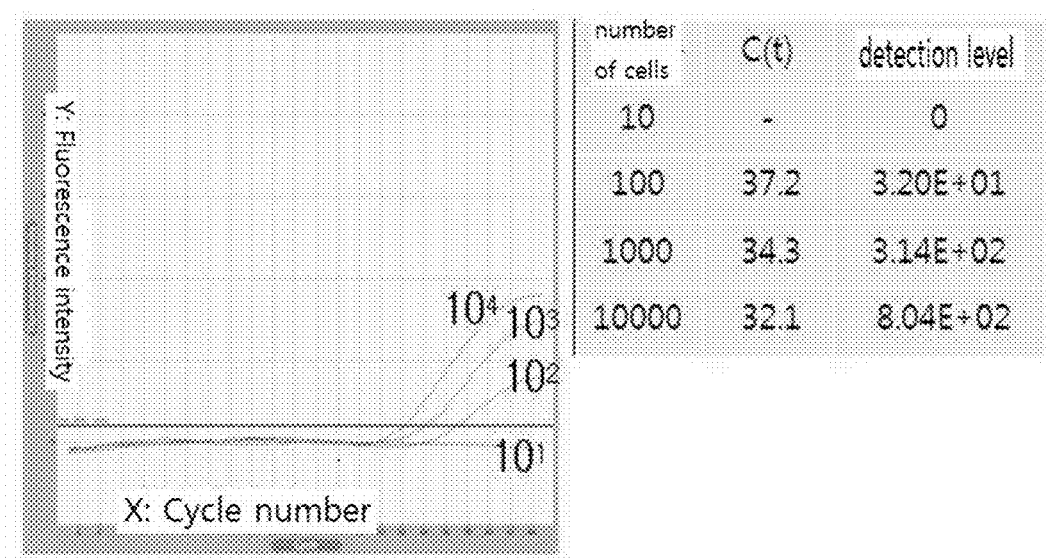

As a result, in the case of the samples comprising the terminated RNA, the hot-start reverse transcription reaction solution was detected in the samples comprising 10 or more Hela cells added to 1 ml of human serum (see FIG. 13*b*). The reaction solutions having no hot start reverse transcription function was detected only in the sample comprising 100 or more Hela cells (FIG. 13*c*). In the case of the samples having no terminated RNA, the hot-start reverse transcription solution was detected in the samples comprising 100 or more Hela cells (FIG. 13*d*). In addition, the reaction having no hot-start reverse transcription function was detected in the samples comprising 1,000 or more Hela cells (FIG. 13*e*).

Thus, it can be seen that the detection limit was increased even by the hot-start reverse transcription reaction alone, but a better effect could be obtained when the hot-start reverse transcription reaction was performed together with RNA termination.

INDUSTRIAL APPLICABILITY

As described above, the composition for hot-start reverse transcription reaction and the composition for hot-start reverse transcription PCR according to the present invention can solve various problems occurring in conventional hot-start reverse transcription reactions and can specifically detect the target RNA with high sensitivity by performing a reverse transcription reaction using PPi and PPase. Thus, the compositions of the present invention can provide a stable kit related to hot-start reverse transcription/hot-start reverse transcription PCR technologies, which can be effectively used as a high-sensitivity RNA diagnostic kit for high-sensitivity detection of RNA.

The invention claimed is:

1. A method of reverse transcription of a template RNA in a sample, the method comprising the steps of:
   mixing the sample with a composition comprising an $Mg^{2+}$ ion, four kinds of dNTPs, a reverse transcription polymerase, a pyrophosphate, and a pyrophosphatase to form a reaction mixture in a single reaction tube, wherein the sample further comprises additional RNAs other than the template RNA; and
   performing a reverse transcription of the reaction mixture to provide a complementary DNA of the template RNA,
   wherein the method inhibits non-specific reverse transcriptions of the additional RNAs.

2. The method of claim 1, wherein the composition comprises the pyrophosphate at a concentration of 0.1-5 mM, and the pyrophosphatase in an amount of 0.005-0.25 U.

3. The method of claim 1, wherein the composition further comprises one or more reverse transcription primers.

4. The method of claim 1, wherein the composition is frozen or dried.

5. The method of claim 1, wherein the composition further comprises an additional template nucleic acid.

6. The method of claim 5, wherein the additional template nucleic acid is an RNA.

7. The method of claim 1, wherein the composition further comprises a dye which is not reactive with a nucleic acid.

8. The method of claim 1, wherein the composition further comprises at least one selected from the group consisting of a polyol, gelatin, bovine serum albumin, Thesit, and PEG-8000.

9. The method of claim 5, wherein the additional template nucleic acid has a nucleic acid polymerization terminator bound to the 3' end thereof to prevent a non-specific nucleic acid polymerization.

10. The method of claim 9, wherein the nucleic acid polymerization terminator is a nucleic acid-like compound that is activated in the form of a triphosphate capable of acting on a nucleic acid polymerase and has groups other than a hydroxyl group at the 3' end.

11. The method of claim 10, wherein the nucleic acid-like compound is at least one selected from the group consisting of 2',3'-dideoxynucleoside 5'-triphosphate, 3'-deoxyadenosine 5'-triphosphate, 3'-azido-3'-deoxythymidine 5'-triphosphate, 1-β-d-Arabinofuranosylnucleoside 5'-Triphosphate, acyclo-guanosine triphosphate, 3'-amino-2'-deoxynucleoside 5'-triphosphate, and 3'-fluoro-3'-deoxynucleoside 5'-triphosphate.

12. A method for detecting a cancer cell in a sample, the method comprising the steps of:
   mixing the sample with a composition comprising a template RNA that has a nucleic acid polymerization terminator bound to the 3' end to prevent a non-specific nucleic acid polymerization, an $Mg^{2+}$ ion, four kinds of dNTPs, a reverse transcription polymerase, nucleic acids, a primer for synthesizing cDNA of the template RNA, a pyrophosphate, a pyrophosphatase, and a primer which binds and amplifies a nucleic acid of a biomarker of the cancer cell to provide a mixture in a single reaction tube;
   performing a reverse transcription and an amplification of the mixture to provide an amplification product; and
   analyzing the amplification product to detect the cancer cell.

13. The method of claim 1, wherein the composition further comprises a DNA polymerase.

14. The method of claim 12, wherein the composition further comprises a DNA polymerase.

* * * * *